US005861482A

United States Patent [19]
Modrich et al.

[11] Patent Number: 5,861,482
[45] Date of Patent: Jan. 19, 1999

[54] SOLUTIONS CONTAINING MISMATCH REPAIR SYSTEM PROTEINS MUTL AND MUTS

[75] Inventors: Paul L. Modrich, Chapel Hill, N.C.; Shin-San Su, Newton, Mass.; Karin G. Au, Durham, N.C.; Robert S. Lahue, Northboro, Mass.; Deani Lee Cooper, Watertown, Mass.; Leroy Worth, Jr., Durham, N.C.

[73] Assignee: Duke University, Durham, N.C.

[21] Appl. No.: 458,733

[22] Filed: Jun. 2, 1995

Related U.S. Application Data

[60] Division of Ser. No. 145,837, Nov. 1, 1993, Pat. No. 5,556,750, and a continuation-in-part of Ser. No. 2,529, Jan. 11, 1993, abandoned, which is a continuation of Ser. No. 350,983, May 12, 1989, abandoned.

[51] Int. Cl.$^6$ ................................................ C07K 14/245
[52] U.S. Cl. ............................................ 530/350; 435/183
[58] Field of Search ........................... 530/380; 435/193, 435/183

[56] References Cited

U.S. PATENT DOCUMENTS 4,794,075  12/1988  Ford et al. .................................. 435/6

FOREIGN PATENT DOCUMENTS

| 2239456 | 7/1993  | United Kingdom . |
| 9302216 | 2/1993  | WIPO . |
| 9320233 | 10/1993 | WIPO . |
| 9322457 | 11/1993 | WIPO . |
| 9322462 | 11/1993 | WIPO . |

OTHER PUBLICATIONS

Lahue et al. Analysis of methyl–directed mismatch repair in vitro. UCLA Symposia in Molecular and Cellular Biology, New Series. vol. 47 (DNA Replication and Recombination), pp. 125–134, 1987.

Pang et al. The mutH, mutL, mutS, and uvrD genes of *Salmoella typhimurium* LT2. Cold Spring HarborSymposia on Quantitative Biology, vol. 49, pp. 597–602, 1984.

Adams et al., "The Biochemistry of the Nucleic Acids," Chapman & Hall pp. 221–223 (1986).

Au et al., "*Escherichia coli* mutY Gene Encodes An Adenine Glycosylase Active on G–A Mispairs," *Proc. Natl. Acad. Sci. USA* 86:8877–8881 (1989).

Au et al., "*Escherichia coli* mutY Gene Product is Required for Specific A–G C–G Mismatch Correction," *Proc. Natl. Acad. Sci. USA* 85:9163–9166 (1988).

Au et al., "Initiation of Methyl–directed Mismatch Repair," *J. Biol. Chem.* 267:12142–12148 (1992).

Bianchi and Radding, "Insertions, Deletions and Mismatches in Heteroduplex DNA Made by RecA Protein," *Cell* 35:511–520 (1983).

Chen and Sigman, "Chemical Conversion of a DNA–Binding Protein Into a Site–Specific Nuclease," *Science* 237:1197–1201 (1987).

Cooper et al., "Methyl–Directed Mismatch Repair is Bidirectional," *J. Biol. Chem.* 268:11823–11829 (1993).

Cotton et al., Reactivity of Cytosine and Thymine In Single––Base–Pair Mismatches with Hydroxylamine and Osmium Tetroxide and Its Application to the Study of Mutations, *Proc. Natl. Acad. Sci. USA* 85:4397–4401 (1988).

Dasgupta and Radding, "Polar Branch Migration Promoted by recA Protein: Effect of Mismatched Base Pairs," *Proc. Natl. Acad. Sci. USA* 79:762–766 (1982).

Fang and Modrich, "Human Strand–Specific Mismatch Repair Occurs by a Bidirectional Mechanism Similar to That of the Bacterial Reaction," *J. Biol. Chem.* 268:11838–11844 (1993).

Grilley et al., "Isolation and Characterization of the *Escherichia coli* mutL Gene Product," *J. Biol. Chem.* 264:1000–1004 (1989).

Grilley et al., "Mechanisms of DNA–Mismatch Correction," *Mutation Research* 236:253–267 (1990).

Grilley et al., "Bidirectional Excision in Methyl–Directed Mismatch Repair," *J. Biol. Chem.* 268:11830–11837 (1993).

Hennighausen and Lubon, "Interaction of Protein With DNA In Vitro," *Guide ot Molecular Cloning Techniques*, Berger and Kimmel eds., 152:721–736 (1987).

Holmes et al., "Strand–specific Mismatch Correction In Nuclear Extracts of Human and Drosophila Melanogaster Cell Lines," *Proc. Natl. Acad. Sci. USA* 87:5837–5841 (1990).

Jiricny et al., "Mismatch–containing Oligonuycleotide Duplexes Bound By the *E. coli* mutS–encoded Protein," *Nucleic Acids Research* 16:7843–7853 (1988).

Lahue et al., "Requirement for d(GATC) Sequences in *Escherichia coli* mutHLS Mismatch Correctiun," *Proc. Natl. Acad. Sci. USA* 84:1482–1486 (1987).

Lahue and Modrich, DNA Mismatch Correction in a Defined System, *Science* 245:160–164 (1989).

Lahue and Modrich, "Methyl–directed DNA Mismatch Repair in *Escherichia coli*," *Mutation Research* 198:37–43 (1988).

Lu et al., "Repair of DNA Base–pair Mismatches in Extracts of *Escherichia coli*," Cold Spring Harbor Laboratory, Cold Spring Harbor Symposia on Quantitative Biology, XLIX:589–596 (1984).

(List continued on next page.)

*Primary Examiner*—Elizabeth C. Kemmerer
*Attorney, Agent, or Firm*—Lyon & Lyon LLP

[57] ABSTRACT

A diagnostic method for detecting a base pair mismatch in a DNA duplex, comprising the steps of contacting at least one strand of a first DNA molecule with the complementary strand of a second DNA molecule under conditions such that base pairing occurs contacting a DNA duplex potentially containing a base pair mismatch with a mispair recognition protein under conditions suitable for the protein to form a specific complex only with the DNA duplex having a base pair mismatch, and not with a DNA duplex lacking a base pair mismatch, and detecting any complex as a measure of the presence of a base pair mismatch in the DNA duplex.

2 Claims, 7 Drawing Sheets

OTHER PUBLICATIONS

Lu and Chang, "Repair of Single Base–Pair Transversion Mismatches of *Escherichia coli* in Vitro: Correction of Certain A/G Mismatches is Independent of dam Methylation and Host mutHLS Gene Functions," *Genetics* 118:593–600 (1988).

Lu and Chang, "A Novel Nucelotide Excision Repair for The Conversion of An A/G Mismatch to C/G Base Pair in *E. coli*," *Cell* 54:805–812 (1988).

Lu, "Influence of GATC Sequences on *Escherichia coli* DNA Mismatch Repair In Vitro," *J. Bacteriology* 169:1254–1259 (1987).

Lu and Hsu, "Detection of Single DNA Base Mutations with Mismatch Repair Enzymes," *Genomics* 14:249–255 (1992).

Lu et al., "Methyl–directed Repair of DNA Base–pair Mismatches in Vitro," *Proc. Natl. Acad. Sci. USA* 80:4639–4643 (1983).

Marx, "DNA Repair Comes Into Its Own," *Science* 266:728–730 (1994).

Modrich, *Molecular Mechanims of DNA—Protein Interaction*, 1986, NIH Grant, Abstract (Source: CRISP).

Modrich, "Mechanisms and Biological Effects on Mismatch Repair," *Ann. Rev. Genet.* 25:229–253 (1991).

Modrich et al., "DNA Mismatch Correction," *Ann. Rev. Biochem.* 56:435–466 (1987).

Modrich, "Mismatch, Repair, Genetic Stability and Cancer," *Science* 266:1959–1960 (1994).

Modrich, "Methyl–directed DNA Mismatch Correction," *J. Biol. Chem.* 264:6597–6600 (1989).

Modrich, *Molecular Mechanisms of DNA—Protein Interaction*, 1986, NIH Grant, Abstract (Source: CRISP).

Myers et al., "Detection of Single Based Substitutions by Ribonuclease Cleavage at Mismatches in RNA:DNA Duplexes," *Science* 230:1242–1246 (1985).

Nelson et al., "Genomic Mismatch Scanning A New Approach to Genetic Linkage Mapping," *Nature Genetics* 4:11–19 (1993).

Pang et al., "Identification and Characterization of the mutL and mutS Gene Products of *Salomonella typhimurium* LT2," *J. Bacteriology* 163:1007–1015 (1985).

Priebe et al., "Nucleotide Sequence of the hexA Gene for DNA Mistmatch Repair in *Streptococus pneumoniae* and Homology of hexA to mutS of *Escherichia coli* and *Salmonella typhimurium*," *J. Bacteriology* 170:190–196 (1988).

Quinones et al., "Expression of the *Escherichia coli* dna Q (mutD) Gene is Inducible," *Mol. Gene Genet.* 211:106–112 (1988).

Rayssiguier et al., "The Barrier to Recombination Between *Escherichia coli* and *Salmonella typhimurium* is Disrupted in Mismatch–Repair Mutants," *Nature* 342:396–401 (1989).

Reenan and Kolodner, "Isolation and Characterization of Two Saccharomyces cervisiae Genes Encoding Homologs of the Bacterial HexA and MutS Mismatch Repair Protein," *Genetics* 132:963–973 (1992).

Shen and Huang, "Effect of Base Pair Mismatches on Recombination Via the RecBCD Pathway," *Mol. Gen. Genet.* 218:358–360 (1989).

Su and Modrich, "*Escherichia coli* mutS–encoded Protein Binds to Mismatched DNA Base Pairs," *Proc. Natl. Acad. Sci. USA* 83:5057–5061 (1986).

Su et al., "Gap Formation is Associated With Methyl––Directed Mismatch Correction Under Conditions of Restricted DNA Synthesis," *Genome* 31:104–111 (1989).

Su et al., "Mispair Specificity of Methyl–directed DNA Mismatch Correction in Vitro," *J. Biol. Chem.* 263:6829–6835 (1988).

Wilchele et al., *Analytical Biochem.* 171:1–32 (1988).

Welsh et al., "Isolation and Characterization of the *Escherichia coli* mush Gene Product," *J. Biol. Chem.* 262:15624–15629 (1987).

V  5'-AAGCTTTCGAG Hind III
C  3'-TTCGAGAGCTC Xho I

| Reaction conditions | Repair (fmol/20 min) | | | |
|---|---|---|---|---|
| Complete | 15 (<1) | 17 (<1) | 8 (<1) | 10 (<1) |
| - Mut H | <1 | 18 | 1 | 9 |
| - Mut L | <1 | <1 | <1 | <1 |
| - Mut S | <1 | <1 | <1 | 1 |
| - SSB | 2 | <1 | <1 | <1 |
| - pol III holoenzyme | <1 | <1 | <1 | <1 |

SOLUTIONS CONTAINING MISMATCH REPAIR SYSTEM PROTEINS MUTL AND MUTS

This application is a division of Ser. No. 08/145,837, filed Nov. 1, 1993, now U.S. Pat. No. 5,556,750, and a continuation-in-part of Modrich et al., U.S. Ser. No. 08/002, 529, filed Jan. 11, 1993, now abandoned, entitled "Methods For Mapping Genetic Mutations" which is a continuation of U.S. Ser. No. 07/350,983, filed May 12, 1989, now abandoned, entitled, "Methods For Mapping Genetic Mutations", each hereby incorporated by reference herein, including drawings.

This work was supported by the U.S. government, namely Grant No. GM23719. The U.S. government may have rights in this invention.

FIELD OF THE INVENTION

The present invention relates to methods for mapping genetic differences among deoxyribonucleic acid ("DNA") molecules, especially mutations involving a difference in a single base between the base sequences of two homologous DNA molecules.

BACKGROUND OF THE INVENTION

The following is a discussion of relevant art, none of which is admitted to be prior art to the appended claims.

Mapping of genetic differences between individuals is of growing importance for both forensic and medical applications. For example, DNA "fingerprinting" methods are being applied for identification of perpetrators of crimes where even small amounts of blood or sperm are available for analysis. Biological parents can also be identified by comparing DNAs of a child and a suspected parent using such means. Further, a number of inherited pathological conditions may be diagnosed before onset of symptoms, even in utero, using methods for structural analyses of DNA. Finally, it is notable that a major international effort to physically map and, ultimately, to determine the sequence of bases in the DNA encoding the entire human genome is now underway and gaining momentum in both institutional and commercial settings.

DNA molecules are linear polymers of subunits called nucleotides. Each nucleotide comprises a common cyclic sugar molecule, which in DNA is linked by phosphate groups on opposite sides to the sugars of adjoining nucleotides, and one of several cyclic substituents called bases. The four bases commonly found in DNAs from natural sources are adenine, guanine, cytosine and thymine, hereinafter referred to as A, G, C and T, respectively. The linear sequence of these bases in the DNA of an individual encodes the genetic information that determines the heritable characteristics of that individual.

In double-stranded DNA, such as occurs in the chromosomes of all cellular organisms, the two DNA strands are entwined in a precise helical configuration with the bases projecting inward and so aligned as to allow interactions between bases from opposing strands. The two strands are held together in precise alignment mainly by hydrogen bonds which are permitted between bases by a complementarity of structures of specific pairs of bases. This structural complementarity is determined by the chemical natures and locations of substituents on each of the bases. Thus, in double-stranded DNA, normally each A on one strand pairs with a T from the opposing strand, and, likewise, each G with an opposing C.

When a cell undergoes reproduction, its DNA molecules are replicated and precise copies are passed on to its descendants. The linear base sequence of a DNA molecule is maintained in the progeny during replication in the first instance by the complementary base pairings which allow each strand of the DNA duplex to serve as a template to align free nucleotides with its polymerized nucleotides. The complementary nucleotides so aligned are biochemically polymerized into a new DNA strand with a base sequence that is entirely complementary to that of the template strand.

Occasionally, an incorrect base pairing does occur during replication, which, after further replication of the new strand, results in a double-stranded DNA offspring with a sequence containing a heritable single base difference from that of the parent DNA molecule. Such heritable changes are called genetic mutations, or more particularly in the present case, "single base pair" or "point" mutations. The consequences of a point mutation may range from negligible to lethal, depending on the location and effect of the sequence change in relation to the genetic information encoded by the DNA.

The bases A and G are of a class of compounds called purines, while T and C are pyrimidines. Whereas the normal base pairings in DNA (A with T, G with C) involve one purine and one pyrimidine, the most common single base mutations involve substitution of one purine or pyrimidine for the other (e.g., A for G or C for T or vice versa), a type of mutation referred to as a "transition". Mutations in which a purine is substituted for a pyrimidine, or vice versa, are less frequently occurring and are called "transversions". Still less common are point mutations comprising the addition or loss of a small number (1, 2 or 3) of nucleotides arising in one strand of a DNA duplex at some stage of the replication process. Such mutations are called small "insertions" or "deletions", respectively, and are also known as "frameshift" mutations in the case of insertion/deletion of one of two nucleotides, due to their effects on translation of the genetic code into proteins. Mutations involving larger sequence rearrangement also do occur and can be important in medical genetics, but their occurrences are relatively rare compared to the classes summarized above.

Mapping of genetic mutations involves both the detection of sequence differences between DNA molecules comprising substantially identical (i.e., homologous) base sequences, and also the physical localization of those differences within some subset of the sequences in the molecules being compared. In principle, it is possible to both detect and localize limited genetic differences, including point mutations within genetic sequences of two individuals, by directly comparing the sequences of the bases in their DNA molecules.

Other methods for detecting differences between DNA sequences have been developed. For example, some pairs of single-stranded DNA fragments with sequences differing in a single base may be distinguished by their different migration rates in electric fields, as in denaturing gradient gel electrophoresis.

DNA restriction systems found in bacteria for example, comprise proteins which generally recognize specific sequences in double-stranded DNA composed of 4 to 6 or more base pairs. In the absence of certain modifications (e.g., a covalently attached methyl group) at definite positions within the restriction recognition sequence, endonuclease components of the restriction system will cleave both strands of a DNA molecule at specific sites within or near the recognition sequence. Such short recognition sequences occur by chance in all natural DNA sequences, once in every few hundred or thousand base pairs, depending on the recognition sequence length. Thus, digestion of a DNA molecule with various restriction endonucleases, followed by analyses of the sizes of the resulting fragments (e.g., by gel electrophoresis), may be used to generate a physical map ("fingerprint") of the locations in a DNA molecule of selected short sequences.

Comparisons of such restriction maps of two homologous DNA sequences can reveal differences within those specific sequences that are recognized by those restriction enzymes used in the available maps. Restriction map comparisons may localize any detectable differences within limits defined ultimately by the resolving power of DNA fragment size determination, essentially within about the length of the restriction recognition sequence under certain conditions of gel electrophoresis.

In practice, selected heritable differences in restriction fragment lengths (i.e., restriction fragment length polymorphisms, "RFLP"s) have been extremely useful, for instance, for generating physical maps of the human genome on which genetic defects may be located with a relatively low precision of hundreds or, sometimes, tens of thousands of base pairs. Typically, RFLPs are detected in human DNA isolated from small tissue or blood samples by using radio-actively labeled DNA fragments complementary to the genes of interest. These "probes" are allowed to form DNA duplexes with restriction fragments of the human DNA after separation by electrophoresis, and the resulting radioactive duplex fragments are visualized by exposure to photographic (e.g., X-ray sensitive) film, thereby allowing selective detection of only the relevant gene sequences amid the myriad of others in the genomic DNA.

When the search for DNA sequence differences can be confined to specific regions of known sequence, the recently developed "polymerase chain reaction" ("PCR") technology can be used. Briefly, this method utilizes short DNA fragments complementary to sequences on either side of the location to be analyzed to serve as points of initiation for DNA synthesis (i.e., "primers") by purified DNA polymerase. The resulting cyclic process of DNA synthesis results in massive biochemical amplification of the sequences selected for analysis, which then may be easily detected and, if desired, further analyzed, for example, by restriction mapping or direct DNA sequencing methods. In this way, selected regions of a human gene comprising a few kbp may be amplified and examined for sequence variations.

Another known method for detecting and localizing single base differences within homologous DNA molecules involves the use of a radiolabeled RNA fragment with base sequence complementary to one of the DNAs and a nuclease that recognizes and cleaves single-stranded RNA. The structure of RNA is highly similar to DNA, except for a different sugar and the presence of uracil (U) in place of T; hence, RNA and DNA strands with complementary sequences can form helical duplexes ("DNA:RNA hybrids") similar to double-stranded DNA, with base pairing between A's and U's instead of A's and T's. It is known that the enzyme ribonuclease A ("RNase A") can recognize some single pairs of mismatched bases (i.e., "base mispairs") in DNA:RNA hybrids and can cleave the RNA strand at the mispair site. Analysis of the sizes of the products resulting from RNase A digestion allows localization of single base mismatches, potentially to the precise sequence position, within lengths of homologous sequences determined by the limits of resolution of the RNA sizing analysis (Myers, R. M. et al., 1985, Science, 230, 1242–1246). RNA sizing is performed in this method by standard gel electrophoresis procedures used in DNA sequencing.

S1 nuclease, an endonuclease specific for single-stranded nucleic acids, can recognize and cleave limited regions of mismatched base pairs in DNA:DNA or DNA:RNA duplexes. A mismatch of at least about 4 consecutive base pairs actually is generally required for recognition and cleavage of a duplex by S1 nuclease.

Ford et al., (U.S. Pat. No. 4,794,075) disclose a chemical modification procedure to detect and localize mispaired guanines and thymidines and to fractionate a pool of hybrid DNA from two samples obtained from related individuals. Carbodiimide is used to specifically derivatize unpaired G's and T's, which remain covalently associated with the DNA helix.

The present invention concerns use of proteins that function biologically to recognize mismatched base pairs in double-stranded DNA (and, therefore, are called "mispair recognition proteins") and their application in defined systems for detecting and mapping point mutations in DNAs. Accordingly, it is an object of the present invention to provide methods for using such mispair recognition proteins, alone or in combination with other proteins, for detecting and localizing base pair mismatches in duplex DNA molecules, particularly those DNAs comprising several kbp, and manipulating molecules containing such mismatches. Additionally, it is an object of this invention to develop modified forms of mispair recognition proteins to further simplify methods for identifying specific bases which differ between DNAs. The following is a brief outline of the art regarding mispair recognition proteins and systems, none of which is admitted to be prior art to the present invention.

Enzymatic systems capable of recognition and correction of base pairing errors within the DNA helix have been demonstrated in bacteria, fungi and mammalian cells, but the mechanisms and functions of mismatch correction are best understood in *Escherichia coli*. One of the several mismatch repair systems that have been identified in *E. coli* is the methyl-directed pathway for repair of DNA biosynthetic errors. The fidelity of DNA replication in *E. coli* is enhanced 100–1000 fold by this post-replication mismatch correction system. This system processes base pairing errors within the helix in a strand-specific manner by exploiting patterns of DNA methylation. Since DNA methylation is a post-synthetic modification, newly synthesized strands temporarily exist in an unmethylated state, with the transient absence of adenine methylation on GATC sequences directing mismatch correction to new DNA strands within the hemimethylated duplexes.

In vivo analyses in *E. coli* have shown that selected examples of each of the different mismatches are subject to correction with different efficiencies. G-T, A-C, G-G and A-A mismatches are typically subject to efficient repair. A-G, C-T, T-T and C-C are weaker substrates, but well repaired exceptions exist within this class. The sequence environment of a mismatched base pair may be an important factor in determining the efficiency of repair in vivo. The mismatch correction system is also capable in vivo of correcting differences between duplexed strands involving a single base insertion or deletion. Further, genetic analyses have demonstrated that the mismatch correction process requires intact genes for several proteins, including the products of the mutH, mutL and mutS genes, as well as DNA helicase II and single-stranded DNA binding protein (SSB). The following are further examples of art discussing this subject matter.

Lu et al., 80 *Proc. Natl. Acad. Sci. USA* 4639, 1983 disclose the use of a soluble *E. coli* system to support mismatch correction in vitro.

Pang et al., 163 *J. Bact.* 1007, 1985 disclose cloning of the mutS and mutL genes of *Salmonella typhimurium*.

The specific components of the *E. coli* mispair correction system have been isolated and the biochemical functions determined. Preparation of MutS protein substantially free of other proteins has been reported (Su and Modrich, 1986, *Proc. Nat. Acad. Sci. U.S.A.,* 84, 5057–5061, which is hereby incorporated herein by reference). The isolated MutS protein was shown to recognize four of the eight possible mismatched base pairs (specifically, G-T, A-C, A-G and C-T mispairs.

Su et al., 263 *J. Biol. Chem.* 6829, 1988 disclose that the mutS gene product binds to each of the eight base pair mismatches and does so with differential efficiency.

Jiricny et al., 16 *Nucleic Acids Research* 7843, 1988 disclose binding of the muts gene product of *E. coli* to synthetic DNA duplexes containing mismatches to correlate recognition of mispairs and efficiency of correction in vivo. Nitrocellulose filter binding assays and band-shift assays were utilized.

Welsh et al., 262 *J. Biol. Chem.* 15624, 1987 purified the product of the MutH gene to near homogeneity and demonstrated the MutH gene product to be responsible for d(GATC) site recognition and to possess a latent endonuclease that incises the unmethylated strand of hemimethylated DNA 5' to the G of d(GATC) sequences.

Au et al., 267 *J. Biol. Chem.* 12142, 1992 indicate that activation of the MutH endonuclease requires MutS, MutL and ATP.

Grilley et al. 264 *J. Biol. Chem.* 1000, 1989 purified the *E. coli* mutL gene product to near homogeneity and indicate that the mutL gene product interacts with MutS heteroduplex DNA complex.

Lahue et al., 245 *Science* 160, 1989 delineate the components of the *E. coli* methyl-directed mismatch repair system that function in vitro to correct seven of the eight possible base pair mismatches. Such a reconstituted system consists of MutH, MutL, and MutS proteins, DNA helicase II, single-strand DNA binding protein, DNA polymerase III holoenzyme, exonuclease I, DNA ligase, ATP, and the four deoxyribonucleoside triphosphates.

Su et al., 31 *Genome* 104, 1989 indicate that under conditions of restricted DNA synthesis, or limiting concentration of dNTPs, or by supplementing a reaction with a ddNTP, there is the formation of excision tracts consisting of single-stranded gaps in the region of the molecule containing a mismatch and a d(GATC) site.

Grilley et al. 268 *J. Biol. Chem.* 11830, 1993, indicate that excision tracts span the shorter distance between a mismatch and the d(GATC) site, indicating a bidirectional capacity of the methyl-directed system.

Holmes et al., 87 *Proc. Natl. Acad. Sci. USA,* 5837, 1990, disclose nuclear extracts derived from Hela and Drosophila melanogaster $K_c$ cell lines to support strand mismatch correction in vitro.

Cooper et al., 268 *J. Biol. Chem.,* 11823, 1993, describe a role for RecJ and Exonuclease VII as a 5' to 3' exonuclease in a mismatch repair reaction. In reconstituted systems such a 5' to 3' exonuclease function had been provided by certain preparations of DNA polymerase III holoenzyme.

Au et al., 86 *Proc. Natl. Acad. Sci. USA* 8877, 1989 describe purification of the MutY gene product of *E. coli* to near homogeneity, and state that the MutY protein is a DNA glycosylase that hydrolyzes the glycosyl bond linking a mispaired adenine (G-A) to deoxyribose. The MutY protein, an apurinic endonuclease, DNA polymerase I, and DNA ligase were shown to reconstitute G-A to G-C mismatch correction in vitro.

A role for the *E. coli* mismatch repair system in controlling recombination between related but non allelic sequences has been indicated (Feinstein and Low, 113 *Genetics* 13, 1986; Rayssiguier, 342 *Nature* 396, 1989; Shen, 218 *Mol. Gen. Genetics* 358, 1989; Petit, 129 *Genetics* 327, 1991). The frequency of crossovers between sequences which differ by a few percent or more at the base pair level are rare. In bacterial mutants deficient in methyl-directed mismatch repair, the frequency of such events increases dramatically. The largest increases are observed in MutS and MutL deficient strains. (Rayssiguier, supra; and Petit, supra.)

Nelson et al., 4 *Nature Genetics* 11, 1993, disclose a genomic mismatch (GMS) method for genetic linkage analysis. The method allows DNA fragments from regions of identity-by-descent between two relatives to be isolated based on their ability to form mismatch-free hybrid molecules.

The method consists of digesting DNA from the two sources with a restriction endonuclease that produces protruding 3' ends. The protruding 3' ends provide some protection from exonuclease III, which is used in later steps. The two sources are distinguished by methylating the DNA from only one source. Molecules from both sources are denatured and reannealed, resulting in the formation of four types of duplex molecules: homohybrids formed from strands derived from the same source and heterohybrids consisting of DNA strands from different sources. Heterohybrids can either be mismatch free or contain base-pair mismatches, depending on the extent of identity of homologous resins.

Homohybrids are distinguished from heterohybrids by use of restriction endonucleases that cleave at fully methylated or unmethylated GATC sites. Homohybrids are cleaved to smaller duplex molecules, while heterohybrid are resistant to cleavage. Heterohybrids containing a mismatch (es) are distinguished from mismatch free molecules by use of the *E. coli* methyl-directed mismatch repair system. The combination of three proteins of the methyl-directed mismatch repair system MutH, MutL, and MutS along with ATP introduce a single-strand nick on the unmethylated strand at GATC sites in duplexes that contain a mismatch. Heterohybrids that do not contain a mismatch are not nicked. All molecules are then subject to digestion by Exonuclease III (Exo III), which can initiate digestion at a nick, a blunt end or a 5' overhang, to produce single-stranded gaps. Only mismatch free heterohybrids are not subject to attack by Exo III, all other molecules have single-stranded gaps introduced by the enzyme. Molecules with single-stranded regions are removed by absorption to benzoylated napthoylated DEAE cellulose. The remaining molecules consist of mismatch-free heterohybrids which may represent regions of identity by decent.

SUMMARY OF THE INVENTION

Applicant has determined that a single DNA base mispair recognition protein can form specific complexes with any of the eight possible mismatched base pairs embedded in an otherwise homologous DNA duplex. It has also been revealed that another mispair recognition protein can recognize primarily one specific base pair mismatch, A-G, and in so doing, it chemically modifies a nucleotide at the site of the mispair. In addition, defined in vitro systems have been established for carrying out methyl-directed mismatch repair processes. Accordingly, the present invention features the use of such mispair recognition proteins and related correction system components to detect and to localize point mutations in DNAs. In addition the invention concerns methods for the analysis and manipulation of populations of DNA duplex molecules potentially containing base pair mismatches through the use of all or part of defined mismatch repair systems.

The invention utilizes five basic methods for heteroduplex mapping analysis, and manipulation: (i) binding of a mismatch recognition protein, e.g., MutS to DNA molecules containing one or more mispairs; (ii) cleavage of a heteroduplex in the vicinity of a mismatch by a modified form of a mismatch recognition protein; (iii) mismatch-provoked cleavage at one or more GATC sites via a mismatch repair system dependent reaction, e.g., MutHLS; (iv) formation of a mismatch-provoked gap in heteroduplex DNA via reactions of a mismatch repair system and (v) labelling of mismatch-containing nucleotides with a nucleotide analog, e.g., a biotinylated nucleotide, using a complete mismatch repair system.

For clarity in the following discussion, it should be noted that certain distinctions exist related to the fact that some proteins that recognize DNA base mispairs are merely DNA binding proteins, while others modify the DNA as a consequence of mispair recognition. Notwithstanding the fact that in the latter situation the protein modifying the DNA may be associated with the DNA only transiently, hereinafter, whether a mispair recognition protein is capable of DNA binding only or also of modifying DNA, whenever it is said that a protein recognizes a DNA mispair, this is equivalent to saying that it "forms specific complexes with" or "binds specifically to" that DNA mispair in double-stranded DNA. In the absence of express reference to modification of DNA, reference to DNA mispair recognition does not imply consequent modification of the DNA. Further, the phrase "directs modification of DNA" includes both cases wherein a DNA mispair recognition protein has an inherent DNA modification function (e.g., a glycosylase) and cases wherein the mispair recognition protein merely forms specific complexes with mispairs, which complexes are then recognized by other proteins that modify the DNA in the vicinity of the complex.

Accordingly, the present invention features a method for detecting base pair mismatches in a DNA duplex by utilizing a mismatch recognition protein that forms specific complexes with mispairs, and detecting the resulting DNA:protein complexes by a suitable analytical method.

In addition to methods designed merely to detect base pair mismatches, this invention includes methods for both detecting and localizing base pair mismatches by utilizing components of mismatch repair system.

The present invention also features mispair recognition proteins which have been altered to provide an inherent means for modifying at least one strand of the DNA duplex in the vicinity of the bound mispair recognition protein.

The present invention also concerns systems utilizing an A-G specific mispair recognition protein, for example, the *E. coli* DNA mispair recognition protein that recognizes only A-G mispairs without any apparent requirement for hemimethylation. This protein, the product of the mutY gene, is a glycosylase which specifically removes the adenine from an A-G mispair in a DNA duplex. Accordingly, this MutY protein is useful for the specific detection of A-G mispairs according to the practice of the present invention.

The invention also includes the combined use of components of a mismatch repair system along with a recombinase protein. The recombinase protein functions to catalyze the formation of duplex molecules starting with single-stranded molecules obtained from different sources, by a renaturation reaction. Such a recombinase protein is also capable of catalyzing a strand transfer reaction between a single-stranded molecule from one source and double-stranded molecules obtained from a different source. In the presence of a base pair mismatch, formation of duplex regions catalyzed by such a recombinase protein is inhibited by components of a mismatch repair system, e.g., *E. coli* MutS and MutL, proteins. Modulation of recombinase activity by components of a mismatch repair system may involve inhibition of branch migration through regions that generate mismatched base pairs. The combination of a DNA mismatch repair system and a recombinase system provides a very sensitive selection step allowing for the removal of molecules containing a base pair mismatch from a population of newly formed heteroduplex molecules. This procedure provides a selection scheme that can be utilized independent of or in conjunction with the actual mismatch repair reaction.

The invention also features two improvements on the genomic mismatch scanning technique (GMS) of Nelson et al. 4 *Nature Genetics* 11, 1993, used to map regions of genetic identity between populations of DNA molecules.

One improvement provided by the invention features an additional selection step, as described above, for determining genetic variation. The genomic mismatch scanning (GMS) method includes one selection step which is carried out after hybrid formation. The present invention includes an additional step that occurs during hybrid formation, through the use of a protein with recombinase activity along with components of a mismatch repair system. The increase in sensitivity for screening for genetic variation provided by the additional selection step makes possible the use of the GMS technique with larger genomes, e.g., man.

A second improvement provided by the invention features the replacement or modification of the exonuclease III digestion step employed in the GMS method. In the GMS procedure exonuclease III is used to degrade all DNA molecules, except mismatch-free heterohybrids, to molecules containing single-stranded regions, which are subsequently removed. Heterohybrids are duplex molecules which are formed in the method from two molecules which were previously base paired with other molecules (i.e., from different sources). In the instant invention this step is replaced by a procedure that employs all or some of the components of a mismatch repair system. Exo III is a 3' to 5' exonuclease specific for double-stranded DNA, which preferably initiates at blunt or 5' protruding ends. In the GMS procedure DNA molecules are digested with restriction enzymes that produce protruding 3' ends. Although molecules containing protruding 3' ends are not preferred substrates for Exo III, such molecules can be subject to limited attack by the enzyme. Thus, even mismatch-free heterohybrids will be degraded to some extent by Exo III, and will be erroneously removed from the final population of molecules representing those of identity-by-descent. The invention employs components of a mismatch repair system along with dideoxy or biotinylated nucleotide, to avoid the use of Exo III and the potential loss of heterohybrids molecules that are mismatch-free. Homohybrids are digested in the presence of helicase II by exoVI RecJ and exo I, e.g., natural exonucleases involved in the mismatch repair reaction. The invention also features a modification of the step utilizing Exo III, consisting of ligation of duplex DNA molecules at dilute concentrations so as to form closed circular monomer molecules, thus removing any 3' ends which may be subject to degradation by Exo III.

The invention includes the use of a mismatch repair system to detect and remove or correct base pair mismatches in a population produced by the process of enzymatic amplification of nucleic acid molecules. DNA polymerase errors that occur during a cycle of enzymatic amplification can result in the presence of mismatched base pair(s) in the population of product molecules. If such errors are perpetuated in subsequent cycles they can impair the value of the final amplified product. The fidelity of the amplification method can be enhanced by including one or more components of a mismatch repair system to either correct the mismatch base pair(s) or to eliminate from the amplified population, molecules that contain mismatch base pair(s). Elimination of molecules containing a base pair mismatch can be accomplished by binding to a protein, such as MutS, or by introduction of a nick in one strand of the duplex so that a full sized product will not be produced in a subsequent round of amplification.

The invention also features methods to remove molecules containing a base pair mismatch through the binding of the mismatch to the components of the mismatch repair system or by the binding of a complex of a mismatch and components of a mismatch repair system to other cellular proteins. Another aspect of the invention for removal of molecules containing a mismatch is through the incorporation of biotin into such a molecule and subsequent removal by binding to avidin.

Another aspect of the invention features use of a mismatch repair system which has a defined 5' to 3' exonuclease function, that is provided by the exonuclease VII or RecJ exonuclease. In other systems a 5' to 3' exonuclease function is provided by exonuclease VII which is present in many preparations of the DNA polymerase III holoenzyme.

The invention also includes kits having components necessary to carry out the methods of the invention.

The mismatch repair systems of the instant invention, e.g., *E. coli,* offer specific and efficient procedures for detection and localization of mismatches and manipulation of DNA containing mismatches that is a reflection of their biological function. All eight possible base pair mismatches are recognized and seven of the eight mismatches are processed and corrected by the system. Although C-C mismatches are not a substrate for repair, MutS does bind weakly to this mispair permitting its detection. In contrast to the electrophoretic migration procedure, the RNase method, or chemical modification procedures, the system does not depend on the destabilization of the DNA helix for detection of mismatches or binding to mismatches. The system features exquisite specificity, and is not subject to non-specific interactions with bases at the ends of linear DNA fragments or non-specific interactions at non-mismatch sites in long molecules.

The detection of fragments containing a mispair is limited only by the intrinsic specificity of the system, for example, detection of better than one G-T mispair per 300 kilobases. Mismatches have been routinely detected with a 6,400 base pair substrate and the system should be applicable to molecules as large as 40–50 kb. This allows for detection of possible single base differences between long DNA sequences, for example, between a complete gene from one individual and the entire genome of another. The invention also enables the localization of any possible single base difference within the sequences of homologous regions of long DNA molecules such as those encoding one or more complete genes and comprising several kbp of DNA.

Several of the methods of the invention result in the covalent alteration of the phosphodiester backbone of DNA molecules. This covalent alteration facilitates analysis of the product DNA molecules especially by electrophoretic methods.

Other features and advantages of the invention will be apparent from the following description of the preferred embodiments thereof, and from the claims.

DESCRIPTION OF PREFERRED EMBODIMENTS

Figure 1:
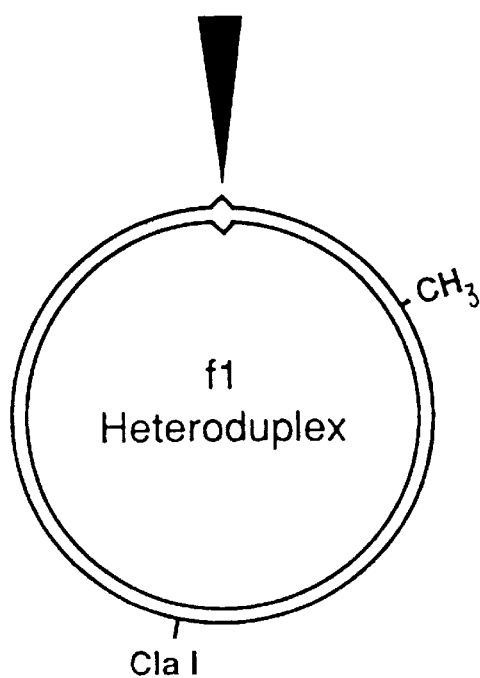
FIG. 1. Heteroduplex substrate for in vitro mismatch correction. The substrate used in some examples is a 6440-bp, covalently closed, circular heteroduplex that is derived from bacteriophage f1 and contains a single base-base mismatch located within overlapping recognition sites for two restriction endonucleases at position 5632. In the example shown a G-T mismatch resides within overlapping sequences recognized by Hind III and Xho I endonucleases (SEQ. ID. NO. 12). Although the presence of the mispair renders this site resistant to cleavage by either endonuclease, repair occurring on the complementary (c) DNA strand yields an A-T base pair and generates a Hind III-sensitive site, while correction on the viral (v) strand results in a G-C pair and Xho I-sensitivity. The heteroduplexes also contain a single d(GATC) sequence 1024 base pairs from the mismatch (shorter path) at position 216. The state of strand methylation at this site can be controlled, thus permitting evaluation of the effect of DNA methylation on the strand specificity of correction.

The invention consists of methods utilizing and kits consisting of components of mismatch repair system to detect, and localize DNA base pair mismatches and manipulate molecules containing such mismatches. The invention also features modified mispair recognition proteins and their utilization in the above-mentioned methods and kits. The invention also includes methods and kits comprising components of a mismatch repair system along with proteins with recombinase activity. The invention also consists of methods to improve the GMS technique to detect regions of homology-by-descent.

Methods for detecting the presence and localization of mismatched base pairs by complex formation with a mismatch recognition protein One embodiment of the invention features a diagnostic method for detecting a base pair mismatch in a DNA duplex. The method comprises the steps of contacting at least one strand of a first DNA molecule with the complementary strand of a second DNA molecule under conditions such that base pairing occurs, contacting a DNA duplex potentially containing a base pair mismatch with a mispair recognition protein under conditions suitable for the protein to form a specific complex only with the DNA duplex having a base pair mismatch., and not with a DNA duplex lacking a base pair mismatch, and detecting the complex as a measure of the presence of a base pair mismatch in the DNA duplex.

By "mismatch" is meant an incorrect pairing between the bases of two nucleotides located on complementary strands of DNA, i.e., bases pairs that are not A:T or G:C.

In the practice of this method, the two DNA's or two DNA samples to be compared may comprise natural or synthetic sequences encoding up to the entire genome of an organism, including man, which can be prepared by well known procedures. Detection of base sequence differences according to this method of this invention does not require cleavage (by a restriction nuclease, for example) of either of the two DNAs, although it is well known in the art that rate of base pair formation between complementary single-stranded DNA fragments is inversely related to their size. This detection method requires that base sequence differences, to be detected as base pair mismatches lie within a region of homology constituting at least about 14 consecutive base pairs of homology between the two DNA molecules, which is about the minimum number of base pairs generally required to form a stable DNA duplex. Either one or both of the strands of the first DNA may be selected for examination, while at least one strand of the second DNA complementary to a selected first DNA strand must be used. The DNA strands, particularly those of the second DNA, advantageously may be radioactively labeled to facilitate direct detection, according to procedures well known in the art.

By "mispair recognition protein" is meant a protein of a mismatch repair system that specifically recognizes and binds to a base pair mismatch, e.g., E. coli MutS.

Methods and conditions for contacting the DNA strands of the two DNAs under conditions such that base pairing occurs are also widely known in the art.

In preferred embodiments of this aspect of this invention, the mispair recognition protein is the product of the mutS gene of E. coli. or species variations thereof, or portions thereof encoding the recognition domain. The protein recognizes all eight possible base pair mismatches, detection of the DNA:protein complex comprises contacting the complexes with a selectively absorbent agent under conditions such that the protein:DNA complexes are retained on the agent while DNA not complexed with protein is not retained and measuring the amount of DNA in the retained complexes, the absorbent agent is a membranous nitrocellulose filter, detection of the DNA:protein complex further includes the step wherein an antibody specific for the base mispair recognition protein is employed, the base mispair recognition protein is the product of the muts gene of S. typhimurium the hexA gene of S. pneumoniae or the MSH1 and MSH2 genes of yeast, and wherein the step for detecting the DNA:protein complex further includes a step wherein the electrophoretic mobility of the DNA:protein complex is compared to uncomplexed DNA.

The ability of the MutS protein to recognize examples of all eight single base pair mismatches within double-stranded DNA, even including C-C mispairs which do not appear to be corrected in vivo, is demonstrated by the fact that MutS protein protects DNA regions containing each mismatch from hydrolysis by DNase I (i.e., by "Dnase I footprint" analyses), as recently reported (Su, S.-S., et al., 1988, *J. Biol. Chem.*, 263, 6829–6835). The affinity of MutS protein for the different mispairs that have been tested varies considerably. Local sequence environment may also affect the affinity of the MutS protein for any given base mispair; in other words, for example, the affinity for two specific cases of A-C mispairs, which are surrounded by different sequences, may not be the same. Nevertheless, no examples of base mispairs have been found that are not recognized by isolated MutS protein. Accordingly, this method of the invention detects all mismatched base pairs.

It should be particularly noted that the DNA duplexes which MutS recognizes are not required to contain GATC sequences and, hence, they do not require hemimethylation of A's in GATC sequences, the specific signal for the full process of methyl-directed mispair correction in vivo; therefore, use of MutS in this method allows recognition of a DNA base mispair in DNAs lacking such methylation, for instance, DNAs isolated from human tissues.

By "species variation" is meant a protein which appears to be functionally and in part, at least, structurally homologous to the E. coli MutS protein. One example of such a protein has also been discovered in a methyl-directed mispair correction system in *Salmonella typhimurium* bacteria (Pang et al., 1985, J. Bacteriol., 163, 1007–1015). The gene for this protein has been shown to complement *E. coli* strains with mutations inactivating the mutS gene and the amino acid sequence of its product shows homology with that of the *E. coli* MutS protein. Accordingly, this *S. typhimurium* protein is also suitable for the practice of this aspect of the present invention. Other organisms, including man, are known to possess various systems for recognition and repair of DNA mispairs, which, as one skilled in the art would appreciate, comprise mispair recognition proteins functionally homologous to the MutS protein. Nuclear extracts derived from Hela and Drosophila melanogaster $K_c$ cell lines has been shown to support efficient strand-specific mismatch correction in vitro (Holmes et al., 1990, *Proc. Natl. Acad. Sci. USA* 87, 5837–5841, which is incorporated herein by reference), and this reaction has been shown to occur by a mechanism similar to that of the bacterial reaction (Fany and Modrich 268 *J. Biol. Chem.* 11838, 1993). Furthermore, genes encoding proteins that are homologous to bacterial MutS at the amino acid sequence level have been demonstrated in human (Fujii and Shimada 264 *J. Biol. Chem.* 10057, 1989) and yeast (Reenan and Kolodner 132 *Genetics* 963, 1992) and *S. pneumoniae* (Priebe et al, 170 *J. Bacteriol.* 190, 1988). Accordingly, it is believed that such DNA base mispair recognition proteins may also be suitable for use in the present invention.

By "protein encoding the recognition domain" is meant a region of the mispair recognition protein which is involved in mispair recognition and binding. Such a domain comprises less than the complete mispair recognition protein.

By a "selectively adsorbent agent" is meant any solid substrate to which protein:DNA complexes are retained on the agent while DNA not complexed with protein is not retained, such agents are known to those skilled in the art. Absent radioactive labeling of at least one strand used to form the DNA duplexes, the DNA in complexes on the filter may be detected by any of the usual means in the art for detection of DNA on a solid substrate, including annealing with complementary strands of radioactive DNA.

The nitrocellulose filter method for detecting complexes of MutS protein with base mispairs in DNA has been reported in detail (Jiricny, J. et al., 1988, *Nuc. Acids Res.* 16, 7843–7853, which is hereby incorporated herein by reference). Besides simplicity, a major advantage of this method for detecting the DNA:protein complex over other suitable methods is the practical lack of a limitation on the size of DNA molecules that can be detected in DNA:protein duplexes. Therefore, this embodiment of this method is in principle useful for detecting single base sequence differences between DNA fragments as large as can be practically handled without shearing.

By "electrophoretic mobility" is meant a method of separating the DNA:protein complexes from DNA that does not form such complexes on the basis of migration in a gel medium under the influence of an electric field. DNA:protein complexes are less mobile than naked DNA. Such methods based on electrophoretic mobility are known to those skilled in the art. The DNA in the DNA:protein complexes may be detected by any of the usual standard means for detection of DNA in gel electrophoresis, including staining with dyes or annealing with complementary strands of radioactive DNA. Detecting complexes comprising the MutS base mispair recognition protein and mispairs in DNA duplexes is also described in the foregoing reference (Jiricny, J. et al., 1988, *Nuc. Acids Res.,* 16, 7843–7853). Under the usual conditions employed in the art for detecting specific DNA:protein complexes by gel electrophoresis, complex formation of a protein with a double-stranded DNA fragment of up to several hundred base pairs is known to produce distinguishable mobility differences.

Antibodies specific for a DNA mispair recognition protein can be prepared by standard immunological techniques known to those skilled in the art.

Other suitable analytical methods for detecting the DNA protein complex include immunodetection methods using an antibody specific for the base mispair recognition protein. For example, antibodies specific for the E. coli MutS protein have been prepared. Accordingly, one immunodetection method for complexes of MutS protein with DNA comprises the steps of separating the DNA:protein complexes from DNA that does not form such complexes by immunoprecipitation with an antibody specific for MutS protein, and detecting the DNA in the precipitate. According to the practice of this aspect of the invention, quantitative immunoassay methods known in the art may be employed to determine the number of single base mispairs in homologous regions of two DNA molecules, based upon calibration curves that can be established using complexes of a given mispair recognition protein with DNA duplexes having known numbers of mispairs.

Another aspect of the invention features a method for detecting and localizing a base pair mismatch in a DNA duplex. The method includes contacting at least one strand of the first DNA molecule with the complementary strand of the second DNA molecule under conditions such that base pairing occurs, contacting the resulting double-stranded DNA duplexes with a mispair recognition protein under conditions such that the protein forms specific complexes with mispairs, subjecting the duplex molecules to hydrolysis with an exonuclease under conditions such that the complex blocks hydrolysis, and determining the location of the block to hydrolysis by a suitable analytic method.

"Hydrolysis with an exonuclease" is a procedure known to those skilled in the art and utilizes enzymes possessing double-strand specific exonuclease activity, e.g., E. coli exonuclease III, RecBCD exonuclease, lambda exonuclease, and T7 gene 6 exonuclease.

By "block to hydrolysis" is meant interference of hydrolysis by the exonuclease. Such protection can result from the mispair recognition protein protecting the DNA to which it is bound.

By "suitable analytical method" is meant any method that allows detection of the block to exonuclease digestion, such analysis of molecules by gel electrophoresis. Such methods are known to those skilled in the art.

Methods for detecting and localizing base pair mismatches by mismatch repair system strand modification reactions In addition to methods that detect base sequence differences, this invention provides methods for both detecting and localizing a base pair mismatch in a DNA duplex. One method includes contacting at least one strand of the first DNA molecule with the complementary strand of the second DNA molecule under conditions such that base pairing occurs, contacting the resulting double-stranded DNA duplexes with a mismatch recognition protein under conditions such that the protein forms specific complexes with mispairs and thereby directs modification of at least one strand of the DNA in the resulting DNA:protein complexes in the vicinity of the DNA:protein complex, and determination of the location of the resulting DNA modification by a suitable analytical method.

By "modification" is meant any alteration for which there is a means of detection, for instance a chemical modification including breaking of a chemical bond resulting in, as examples, cleavage between nucleotides of at least one DNA strand or removal of a base from the sugar residue of a nucleotide. Specific means for modifying DNAs in the vicinity of the DNA:protein complex are provided below for several embodiments of this aspect of the invention, together with interpretations of the phrase "in the vicinity of", as appropriate to the practical limitations of the modification approach in each instance.

Suitable analytical methods for determining the location of the modification are known to those skilled in the art. Such a determination involves comparison of the modified DNA molecule with the homologous unmodified DNA molecule.

In preferred embodiments of this aspect of the invention, the mispair recognition protein is the product of the mutS gene of E. coli or another functionally homologous protein; the step in which the DNA is modified in the vicinity of the DNA:protein complex further comprises contacting the DNA:MutS protein complex with a defined set or subset of E. coli DNA mismatch repair proteins (comprising E. coli MutH, MutL, DNA helicase II, single-stranded DNA binding protein, DNA polymerase III holoenzyme, exonuclease I, and exonuclease VII (or RecJ exonuclease), or species variations of these activities), ATP and one or more dideoxynucleoside-5'-triphosphates or in the absence of exogenous deoxyribonucleoside-5'-triphosphate under conditions that produce a discontinuity in one or both strands of the DNA duplex in the vicinity of the mismatch.

DNA used in such an analysis are to be unmethylated or hemimethylated at on the 6-position of the adenine base in GATC sequences. With the exception of DNAs from some bacterial species, the chromosomes of most organisms naturally lack this modification. In those cases where hemimethylation of otherwise GATC unmodified molecules is desired, this can be accomplished by use of E. coli Dam methylase as is well known in the art. Symmetrically methylated DNA prepared by use of this enzyme is denatured and subsequently reannealed with single-stranded sequences representing an homologous (or largely so) DNA. If necessary, hemimodified molecules produced by this renaturation procedure can be separated from unmethylated is symmetrically methylated duplexes which can also result from the annealing procedure. As is well known in the art, this can be accomplished by subjecting annealed products to cleavage by DpnI and MboI endonucleases. The former activity cleaves symmetrically methylated duplex DNA at GATC sites while unmodified duplex DNA is subject to double strand cleavage only at unmodified GATC sites by the latter activity. Since hemimodified DNA is resistant to double strand cleavage by both DpnI and MboI, desired hemimethylated products can be separated on the basis of size from the smaller fragments produces by DpnI and MboI cleavage, for example by electrophoretic methods.

By "discontinuity in one or both strands of the DNA duplex" is meant a region which consists of a break in the phosphodiester backbone in one or both strands, or a single-stranded gap in a duplex molecule.

One aspect of this preferred embodiment involves contacting the DNA:MutS protein complex with E. coli MutL and MutH proteins (or species variations thereof) in the presence of ATP and an appropriate divalent cation cofactor (eg., $Mg^{2+}$) so that mismatch-containing molecules will be subject to incision at one or more GATC sites in the vicinity of the mispair. Such incision events can be monitored by a suitable analytic method for size detection such as electrophoresis under denaturing condition.

A second aspect of this preferred embodiment involves contacting the DNA:MutS complex with a defined E. coli mismatch correction system consisting of E. coli MutH, MutL, DNA helicase II, single-stranded DNA binding protein, DNA polymerase III holoenzyme, exonuclease I, and exonuclease VII (or RecJ exonuclease), or species variants of these activities, ATP in the absence of exogenous deoxyribonucleoside-5'-triphosphates or in the presence of one or more dideoxynucleoside-5'-triphosphates such that single-stranded gaps are produced in the vicinity of the complexed protein; the method for determining the location of the single-stranded gaps with the DNA duplex further includes analysis of electrophoretic mobility of treated samples under denaturing conditions of the steps of cleaving the DNA with a single-stranded specific endonuclease, and comparing the electrophoretic mobilities of the cleaved fragments with unmodified DNA fragments under nondenaturing conditions; the step for modifying the DNA duplex in the vicinity of the complexed protein comprises contacting the complexes with proteins of a mismatch repair system, ATP and a divalent cation under conditions such that an endonucleolytic incision is introduced at one or more GATC sequences in the duplex molecule.

An example of a complete defined mismatch correction system comprises the following purified components: E. coli MutH, MutL, and MutS proteins, DNA helicase II, single-stranded DNA binding protein, DNA polymerase III holoenzyme, exonuclease I, DNA ligase, ATP, and the four deoxynucleoside-5'-triphosphates. This set of proteins can process seven of the eight base-base mismatches in a strand-specific reaction that is directed by the state of methylation of a single GATC sequence located 1 kilobase from the mispair. This defined system is described further in Example 1, below. The 5' to 3' exonuclease function can either be supplied by either DNA polymerase III holoenzyme preparations that contain this activity or as a separate defined component consisting of exonuclease VII or RecJ exonuclease. It should be noted that the lack of ability to repair C-C base mispairs in this embodiment of this aspect of the present invention is not a major limitation of the method for detecting all possible base sequence differences between any two naturally occurring DNA sequences because mutations that would give rise to a C-C mispair upon hybridization would also give rise to a G-G mismatch when the complementary strands are hybridized.

For the purpose of generating single-stranded gaps in the vicinity of the DNA:MutS protein complexes, DNA duplexes containing mispaired base pairs are contacted with the defined mismatch correction system under the standard conditions described in Example 1, Table 3 (Complete reaction), except for the following differences: (i) exogenous dNTPs are omitted; or (ii) 2', 3'-dideoxynucleoside-5'-triphosphates (ddNTPs) at suitable concentrations (10 to 100 $\mu$M) are substituted for dNTPs; or (iii) reactions containing dNTPS are supplemented with ddNPPs at a suitable concentration to yield a chain termination frequency sufficient to inhibit repair of single-strand gaps. In cases (i)–(iii) DNA ligase may be omitted from the reaction. In cases (ii) and (iii) all four ddNTPs may be present; however, it is expected that the presence of one, two, or three ddNTPs will prove sufficient to stabilize single strand gaps via chain termination events. While it is expected that most applications of these gap forming protocols will utilize MutH, it is pertinent to note that the requirement of methyl-direct strand incision by MutH may be obviated by provision of a single-strand nick by some other means within the vicinity of the mispair, as described in Example 1, FIG. 5. A suitable means for inducing such nicks in DNA is limited contact with a nuclease, Dnase I, for example; under conditions that are well known in the art, this approach creates nicks randomly throughout double-stranded DNA molecules at suitable intervals for allowing the mismatch correction system to create single-stranded gaps in the vicinity of a mispair anywhere in the DNA.

It should be noted that in this embodiment of this method for localizing mismatch base pairs, "in the vicinity of" a base mispair is defined practically by the size of the single-strand gaps typically observed under above conditions, namely up to about one kbp from the mismatched base pair.

By "determining the location of the single-stranded gaps within the DNA duplex" entails the steps of: (i) Cleaving the DNA with at least one restriction endonuclease (either prior or subsequent to contact of the preparation with mismatch repair activities) followed by comparison of electrophoretic mobilities under denaturing conditions of the resulting modified DNA fragments with DNA restriction fragments not contacted with the defined mismatch correction system; or (ii) Cleaving the DNA with at least one restriction endonuclease and with a single-strand specific endonuclease, followed by comparison of the electrophoretic mobilities under native conditions of the resulting modified DNA fragments with DNA restriction fragments not contacted with the defined mismatch correction system. Suitable single-strand specific endonucleases include the S1 single-stranded specific nuclease, for example, or other functionally similar nucleases well known in the art. In the cases of either (i) of (ii), additional restriction mapping may be performed as needed to further localize any fragment modifications observed in initial application of the method, until, if desired, a restriction fragment of convenient size for direct sequence determination is obtained for direct comparisons of sequences of the two DNA molecules in the vicinity of the base sequence difference.

By "proteins of a mismatch repair system" are meant a protein that contains a GATC endonuclease, a mispair recognition protein, and proteins that participate in the activation of the GATC endonuclease.

By "divalent cation: is meant a cofactor for the GATC endonucleases, e.g., $MgCl_2$.

By "endonucleolytic incision: is meant cleavage of a DNA fragment containing a mismatched base pair at unmethylated of hemimethylated GATC sequences in the vicinity of a mismatch.

"Size fractionation by electrophoretic mobility under denaturing conditions" is a procedure well know by those skilled in the art. Gel Electrophoresis can either be conventional or pulse-field.

Modification of mispair recognition proteins and uses

The present invention also includes forms of mispair recognition proteins which have been altered to provide means for modifying at least one strand of the DNA duplex in the vicinity of the bound mispair recognition protein.

In preferred embodiments of this aspect of the invention, the altered mispair recognition protein is the modified product of the muts gene of E. coli or is another functionally homologous modified protein to which is attached an hydroxyl radical cleaving function; the altered mispair recognition protein may comprise only a segment of the native molecule containing the mispair recognition domain; the hydroxyl radial cleaving function is selected from the group consisting of the altered mispair recognition protein wherein the hydroxyl radical cleaving function is selected from the group consisting of the 1,10-phenanthroline-copper complex, the EDTA iron complex, and the copper binding domain of serum albumin; the altered mispair recognition protein is the product of the mutS gene of E. coli or of another functionally homologous protein to which is attached attachment a DNA endonuclease activity capable of cleaving double-stranded DNA; the endonuclease activity is provided by the DNA cleavage domain of FokI endonuclease.

By "altered mispair recognition protein" is meant a mispair recognition protein that not only recognizes and binds to a base pair mismatch, but possess the ability to modify a strand of a DNA molecule containing such a mismatch.

Several methods for attaching an hydroxyl radical cleaving function to a DNA binding protein are known in the art. For example, lysyl residues may be modified by chemically attaching the 1,10-phenanthroline-copper complex to lysine residues, resulting in conversion of a DNA binding protein into a highly efficient site-specific nuclease that cleaved both DNA strands (in the presence of hydrogen peroxide as a coreactant) within the 20 base pair binding site of the protein, as determined by DNase I footprinting (C.-H. Chen and D. S. Sigman, 1987, Science, 237, 1197). Chemical attachment of an EDTA-iron complex to the amino terminus of another DNA binding protein similarly produced a sequence specific DNA cleaving protein that cut both strands of the target DNA within a few bases of recognition site of similar size (J. P. Sluka, et al., 1987, Science, 235, 777).

An alternate means for attaching the hydroxyl radical cleaving function to this same protein involved extension of the amino terminus with the three amino acids, Gly-Gly-His, which is consensus sequence for the copper-binding domain of serum albumin (D. P. Hack et al., 1988, J. Am. Chem. Soc., 110, 7572–7574). This approach allows for preparation of such an artificial DNA cleaving protein directly by recombinant methods, or by direct synthesis using standard solid phase methods, when the peptide is sufficiently short as it was in this case (55 residues including the 3 added amino acids), thereby avoiding the need for an additional chemical modification step of the reagent which is both time consuming and difficult in large scale production. In contrast to the EDTA-iron complex, the particular peptide sequence constructed in this instance cleaved only one example out of four recognition sites in different sequence environments.

Nevertheless, one skilled in the art of protein engineering would appreciate that this general approach for converting a DNA binding protein into a DNA cleaving protein by attachment of an hydrogen radical cleavage function is widely applicable. Hence, DNA base mispair recognition proteins which normally only bind to DNA are modified to cleave DNA by attachment of an hydroxyl radical cleavage function, according to the practice of this aspect of this invention, without undue experimentation, by adjustment of appropriate variables taught in the art, particularly the chemical nature and length of the "spacer" between the protein and the metal binding site.

Additional altered forms of mispair recognition proteins that modify at least one strand of the DNA in a DNA:protein complex in the vicinity of the bound protein according to the present invention include proteins comprising the portions or "domains" of the unmodified base mispair recognition enzymes that are essential for binding to a DNA mispair. These essential DNA binding domains further comprise peptide sequences that are most highly conserved during evolution; such conserved domains are evident, for example, in comparisons of the sequences of the E. coli MutS protein with functionally homologous proteins in S. typhimurium and other structurally similar proteins. Accordingly, peptide sequences of a DNA base mispair recognition protein that are protected from proteases by formation of specific complexes with mispairs in DNA and, in addition or in the alternative, are evolutionarily conserved, form the basis for a particularly preferred embodiment of this aspect of the present invention, since such peptides constitute less than half the mass of the intact protein and, therefore, are advantageous for production and, if necessary, for chemical modification to attach a cleavage function for conversion of the DNA binding protein into a DNA cleavage protein specific for sites of DNA base mispairs.

The DNA cleavage domain of FokI endonuclease has been defined (Li et al, 1992. Proc. Natl. Acad. Sci. U.S.A., 89: 4275).

Another embodiment of this aspect of the invention consists of a method for detecting and localizing a base pair mismatch within a DNA duplex, including the steps of contacting at least one strand of the first DNA molecule with the complementary strand of the second DNA molecule under conditions such that base pairing occurs; contacting resultant duplex DNA molecules with an altered mispair recognition protein, under conditions such that the protein forms specific complexes with a mispair and thereby directs modification of at least one strand of the DNA in the resulting DNA protein complexes in the vicinity of the DNA protein complex, and determining the location of the modification of the DNA by a suitable analytic method.

In the detection and localization of a base pair mismatch method according to this embodiment which employs an altered mispair recognition protein, and the modification comprises double-stranded cleavage of the DNA within the vicinity of any base mispair wherein the "vicinity" substantially corresponds to the sequence of DNA protected by the binding of the protein to a base mispair, generally within about 20 base pairs. A single-strand specific nuclease, S1, for instance, may be used to augment cleavage by the modified base mispair recognition protein in the event that a single-strand bias is suspected in the cleavage of any DNAs with which the protein forms a specific complex. Alternatively, DNA's subject to cleavage by the modified mispair recognition protein may be analyzed by electrophoresis under denaturing conditions. Location of the modification is by suitable analytical methods known to those skilled in the art. Methods utilizing mismatch repair systems to detect A-G base pair mismatches In a preferred embodiment, a method for detecting and localizing A-G mispairs in a DNA duplex, includes the steps of contacting at least one strand of the first DNA molecule with the complementary strand of the second DNA molecule under conditions such that base pairing occurs; contacting resultant duplex DNA molecules with a mispair recognition protein that recognizes A-G mispairs and an apurinic endonuclease or lyase under conditions such that in the presence of a mismatch an endonucleolytic incision is introduced in the duplex molecule, and determining the location of the incision by a suitable analytic method.

In preferred embodiments the A-G mispair recognition protein is the product of the mutY gene of E. coli; and the analytical method includes gel electrophoresis.

The present invention also comprises DNA mispair recognition protein that recognizes primarily A-G mispairs without any apparent requirement for hemimethylation. One example of this protein is the product of the mutY gene of E. coli, is a glycosylase which specifically removes the adenine from an A-G mispair in a DNA duplex. The MutY protein has been purified to near homogeneity by virtue of its ability to restore A-G to C•G mismatch correction to cell-free extracts (K. G. Au et al., Proc. Nat. Acad. Sci. U.S.A., 85, 9163, 1988) of a muts mutY double mutant strain of E. coli, as described in Example 2, below. Its electrophoretic migration in the presence of dodecyl sulfate in consistent with a molecular weight of 36 kDa, and it apparently exists as a monomer in solution. MutY, an apurinic (AP) endonuclease, DNA polymerase I, and DNA ligase are sufficient to reconstitute MutY-dependent, A-G to C•G repair in vitro. A DNA strand that has been depurinated thusly by the MutY protein is susceptible to cleavage by any of several types of AP endonuclease or lyase (e.g., human AP endonuclease II) or by piperidine, under conditions that are well known in the art. The cleavage products are then analyzed by gel electrophoresis under denaturing conditions. Accordingly, this MutY protein is useful in a method for the specific detection and localization of A-G mispairs, according to the practice of the present invention, and hence identification of A•T to C•G or G•C to T•A mutations.

Sources of DNA fragments to be analyzed

In another embodiment of the invention, DNA molecules are obtained from the following sources: different individuals of the same species, individuals of different species, individuals of different kingdoms, different tissue types, the same tissue type in different states of growth, different cell types, cells of the same type in different states of growth, and cells of the same origin in different stages of development, and cells of the same type that may have undergone differential somatic mutagenesis, e.g., one class of which may harbor percancerous mutation(s).

In a preferred embodiment, the DNA molecules comprise a probe sequence that has been at least partially characterized.

By "probe sequence that has been at least partially characterized" is meant a DNA molecule from any source that has been characterized by restriction mapping or sequence analysis, such techniques are known to those skilled in the art.

Kits comprising a mispair recognition protein

Another aspect of the invention features assay kits designed to provide components to practice the methods of the invention.

In one aspect the invention features an assay kit for detecting a base pair mismatch in a DNA duplex. The kit comprises one or more of the following components: an aliquot of a mispair recognition protein, an aliquot of control oligonucleotides, and an exonuclease.

In a preferred embodiment the mispair recognition protein is the product of the muts gene of $E.$ $coli.$ By "control oligonucleotides" is meant oligonucleotides for assaying the binding of the mismatch repair protein to a base pair mismatch. One set of oligonucleotides are perfectly homologous (negative control) and thus are not bound by the mispair recognition protein. Another set of oligonucleotides containing a base pair mismatch (positive control) and thus are bound by the mispair recognition protein.

"By "exonuclease" is meant enzymes possessing double-strand specific exonuclease activity, e.g., $E.$ $coli$ exonuclease III, RecBCD exonuclease, lambda exonuclease, and T7 gene 6 exonuclease.

Another aspect of the invention features an assay kit for detecting and localizing a base pair mismatch in a DNA duplex. The kit comprises one or more of the following components: an aliquot of all or part of a mismatch repair system, an aliquot of dideoxynucleoside triphosphates; and a single-strand specific endonuclease.

By "all or part of a mismatch repair system" is meant either the complete system which is capable of repairing a base pair mismatch, for example, the three $E.$ $coli$ proteins MutH, MutL, and MutS, DNA helicase II, single-strand binding protein, DNA polymerase III, exonuclease I, exonuclease VII or RecJ exonuclease, DNA ligase and ATP, or only the three proteins MutH, MutL, and MutS, along with ATP such that an endonucleolytic incision is made at a GATC site, with no subsequent repair reaction taking place.

In preferred embodiments the mismatch repair system includes: the products of the $E.$ $coli$ mutH, mutL, and mutS genes, or species variations thereof, DNA helicase II, single-strand DNA binding protein, DNA polymerase III holoenzyme, exonuclease I, exonuclease VII or RecJ exonuclease, DNA ligase, and ATP, the mismatch repair system includes only the products of the $E.$ $coli$ mutH, mutL, and mutS genes, or species variations thereof, and ATP.

Another embodiment of the invention feature an assay kit for detecting and localizing a base pair mismatch in a DNA duplex comprising an aliquot of a modified mispair recognition protein.

In a preferred embodiment the mispair recognition protein is the product of the muts gene of $E.$ $coli.$ A further embodiment of this aspect of the invention features an assay kit for detecting and localizing an A-G mispair within a DNA duplex. The kit comprises one or more of the following components: an aliquot of an A-G mispair recognition protein; and an aliquot of an apurinic endonuclease or lyase.

In a preferred embodiment the A-G mispair recognition protein is the product of the MutY gene of $E.$ $coli$ Methods utilizing mismatch repair systems and recombinase proteins In a further aspect, the invention features a method for eliminating DNA molecules containing one or more mismatches from a population of heterohybrid duplex DNA molecules formed by base pairing of single-stranded DNA molecules obtained from a first source and a second source. The method includes digesting genomic DNA from the first and the second source with a restriction endonuclease, methylating the DNA of one of the sources, denaturing the DNA from one or both sources, mixing the DNA molecules from the first and the second source in the presence of a recombinase protein, proteins of a mismatch repair system that modulate the recombinase protein, single-strand binding protein, and ATP under conditions such that DNA duplexes form in homologous regions of the DNA molecules from the first and the second source and the presence of a base pair mismatch results in regions that remain single-stranded, and removing molecules that contain single-stranded regions from the population.

By "heterohybrid" is meant a duplex DNA molecule that consists of base-paired strands originating from two different sources, such that one strand of the duplex is from one source (first source) and the other strand is from another source (second source).

The "source" of DNA molecules designates the origin of the genomic DNA used in the method. The first and second sources are different, i.e., not from the same cell of the same individual.

By "restriction endonuclease" is meant an enzyme which recognizes specific sequences in double-stranded DNA and introduces breaks the phosphodiester backbone of both strands. For use in the current invention restriction endonucleases that digest genomic DNA or cDNA into fragments of approximately 4 to 20 kilobases are preferred.

By "methylating" is meant the process by which a methyl groups is attached to the adenine residue of the sequence "GATC". This reaction is carried by enzymes well known in the art, such as the DAM system of $E.$ $coli.$ By "denaturing" is meant the process by which strands of duplex DNA molecules are no longer based paired by hydrogen bonding and are separated into single-stranded molecules. Methods of denaturation are well known to those skilled in the art and include thermal denaturation and alkaline denaturation.

By "recombinase protein" is meant a protein that catalyzes the formation of DNA duplex molecules. Such a molecule is capable of catalyzing the formation of duplex DNA molecules from complimentary single-stranded molecules by renaturation or by catalyzing a strand transfer reaction between a single-stranded molecule and a double-stranded molecule. Examples of such a protein are the RecA proteins of *E. coli* and *S. typhimurium*.

By "proteins of a mismatch repair system that modulate the recombinase protein" are meant components of a system which recognizes and corrects base pairing errors in duplex DNA molecules and also influence the activity of a recombinase protein. For example, a mispair recognition protein, e.g., MutS, and a protein that interacts with the mismatch repair protein, e.g., MutL, together inhibit duplex formation catalyzed by the recombinase protein in the presence of a base pair mismatch. Such modulation of the recombinase protein results in single-stranded regions downstream of the base pair mismatch.

In preferred embodiments, the recombinase protein is the *E. coli* RecA protein, the mismatch repair system is from *E. coli* and the components are the MutS and MutL proteins, the sources of DNA are different individuals of the same species, individuals of different species, individuals of different kingdoms, different tissue types, the same tissue type in different states of growth, different cell types, cells of the same type in different states of growth, cells of the same origin in different stages of development, and cells of the same origin that may have undergone differential somatic mutagenesis, the method of removing molecules containing single-stranded regions is by chromatography on benzoylated naphthoylated DEAE, the method of removing molecules containing single-stranded regions is by treatment with a single-strand specific nuclease.

The MutS, MutL protein, along with single-strand binding protein and ATP are involved in modulation of the *E. coli* RecA protein in catalyzing heteroduplex formation.

The method for removing molecules containing single-strands from double-stranded molecules by the use of chromatography with benzoylated naphthoylated DEAE is well know to those skilled in the art.

By "single strand specific nuclease" is meant an enzyme that specifically degrades single-stranded regions of DNA molecules and do not degrade double stranded regions. Examples of such nucleases are: S1, mung bean, T7 gene 3 endonuclease and P1 nuclease.

In another aspect, the invention features a method for eliminating DNA molecules containing one or more mismatches from a population of heterohybrid duplex DNA molecules formed by a strand transfer reaction between duplex DNA molecules obtained from a first source and denatured DNA molecules from a second source. The method includes digesting genomic DNA from the first and the second source with a restriction endonuclease, methylating the DNA of one of the sources, denaturing the DNA from the second source, mixing the DNA molecules from the first and the second source in the presence of a protein which catalyzes strand transfer reactions, proteins of a mismatch repair system that modulate the protein with strand transfer activity, single strand binding protein, and ATP under conditions such that DNA heteroduplexes form in homologous regions of the DNA molecules from the first and the second source by strand transfer reaction and the presence of a base pair mismatch results in regions that remain single-stranded, and removing molecules that contain the single-stranded regions from the population.

By "strand transfer reaction is meant" a three strand reaction between duplex DNA from one source and single-stranded DNA from another source in which one strand of the duplex is displaced the by a single-stranded molecule.

By "a protein which catalyzes strand transfer reaction" is meant proteins such as: RecA, homologs of RecA, and proteins with branch migration enhancing activities such as RuvA, RuvB, RecG.

In preferred embodiments, the strand transferase protein is the *E. coli* RecA protein, the mismatch repair system is from *E. coli* and the components are the MutS and MutL proteins, the sources are different individuals of the same species, individuals of different species, individuals of different kingdoms, different tissue types, the same tissue type in different states of growth, different cell types, cells of the same type in different states of growth, and cells of the same origin in different stages of development, cells of the same origin that may have undergone differential somatic mutagenesis (e.g., normal as opposed to pre-tumor cells), a probe sequence that has been at least partially characterized, the method of removing molecules containing single-stranded regions is by chromatography on benzoylated naphthoylated DEAE, the method of removing molecules containing single-stranded regions is by treatment with a single strand specific nuclease.

Methods of improving the Genomic Mismatch Scanning technique

In another aspect the invention features the utilization of a recombinase or strand transferase and proteins of a mismatch repair system that modulate the recombinase or strand transferase, in the hybridization step of the genomic mismatch scanning technique. Formation of duplex molecules catalyzed by a recombinase or strand transferase protein which is modulated by components of a mismatch repair system, provide an additional selection step in the GMS method.

By "genomic mismatch scanning" is meant a technique to identify regions of genetic identity between two related individuals. Such a technique has been described by Nelson et al, 4 *Nature Genetics* 11, 1993.

In a further embodiment the invention features a method of genomic mismatch scanning such that heterohybrid DNA molecules containing a base pair mismatch are removed, without the use of exonuclease III. The method comprises the steps of contacting a population of heterohybrid DNA molecules potentially containing base pair mismatches with all the components of a DNA mismatch repair system in the absence of dNTP's or in the presence of one or more dideoxy nucleoside triphosphates under conditions such that single-stranded gaps are generated in DNA fragments that contained a base pair mismatch and removing the molecules containing single-stranded gaps.

In preferred embodiments the DNA mismatch repair system is the *E. coli* methyl-directed mismatch repair system; removal of molecules containing single-stranded regions is by chromatography on benzoylated naphthoylated DEAE; removal of molecules containing single-stranded regions is by treatment with a single-strand specific nuclease.

In a further embodiment, the invention features another variation of the method of genomic mismatch scanning such that heterohybrid DNA molecules containing base pair mismatches are removed, without the use of exonuclease III. The method comprises the steps of contacting a population of heterohybrid DNA molecules potentially containing base pair mismatches with all the components of a DNA mismatch repair system and biotinylated nucleoside triphosphates under conditions such that biotinylated nucleotides are incorporated into DNA fragments that contained a base pair mismatch and, removing the molecules containing biotinylated molecules by binding to avidin.

Substitution with biotinylated nucleotides and binding of molecules that have incorporated these nucleotides are procedures well known to those skilled in the art. This procedure allows fractionation of a population of hybrid DNA molecules into two fractions: (i) A mismatch free fraction which fails to adhere to avidin; and (ii) A population that originally contained mispairs and which binds to avidin. The former can be utilized in the GMS procedure. The latter, avidin-bound class can be employed for other purposes. For example, when prepared using heterohybrid DNA produced by annealing DNA from two related haploid organisms the biotinylated sequences correspond to those DNA regions that vary genetically between the two organisms. Such sequences can thus be applied to determination of the molecular basis of genetic variation of organisms in question, e.g., pathogenic versus nonpathogenic microbial subspecies.

In a preferred embodiment the mismatch repair system is the methyl-directed mismatch repair system of E. coli.

In a further embodiment, the invention features a method of genomic mismatch scanning such that duplex DNA molecules are subject to exonuclease III digestion only after ligation into monomer circles.

By "ligation into monomer circles" is meant ligation of molecules under conditions of dilute concentration such that ends of the same molecule become ligated. Such a procedure is known to those skilled in the art. In these methods it is advantageous sometimes to separate molecules having mismatches from those which do not. By use of appropriate separation procedures both such populations of molecules can be selected.

Methods applying mismatch repair stems to populations of amplified molecules

In another aspect, the invention features a method for correcting base pair mismatches in a population of DNA duplexes that have been produced by enzymatic amplification potentially containing one or more base pair mismatches. The method includes contacting the population of DNA duplexes with a DNA methylase and a mismatch repair system such that base pair mismatches are corrected.

By "enzymatic amplification" is meant a reaction by which DNA molecules are amplified. Examples of such reactions include the polymerase chain reaction and reactions utilizing reverse transcription and subsequent DNA amplification of one or more expressed RNA sequences.

By "mismatch repair system" is meant a complete system such that base pair mismatches are detected and corrected.

In a preferred embodiment, the mismatch repair system is the methyl-directed mismatch repair system of E. coli. Components of the defined system capable of correcting mismatches include MutH, MutL, and MutS proteins, DNA helicase II, single-strand binding protein, DNA polymerase III holoenzyme, exonuclease I, exonuclease VII or RecJ, DNA ligase, ATP and four deoxynucleoside triphosphates.

In a further aspect, the invention features a method for removing DNA molecules containing one or more base pair mismatches in a population of molecules that have been produced by enzymatic amplification potentially containing one or more base pair mismatches. The method includes contacting a population of enzymatically amplified molecules with components of a mismatch repair system under conditions such that one or more components of the repair system form a specific complex with a base pair mismatch contained in a DNA duplex and removing DNA duplexes containing the complex from the population of duplex molecules.

By "complex" is meant the result of specific binding of at least one component of mismatch repair system to a base pair mismatch.

In a preferred embodiment, the mismatch repair system is the E. coli methyl-directed mismatch repair system, the component of the system is the MutS protein, the MutS protein is affixed to a solid support and removal of the DNA duplex containing the complex is by binding to this support.

Methods of attachment of proteins to solid support systems and use of those systems to perform chromatography so as to remove specific molecules are well known to those skilled in the art.

In another embodiment, the invention features a method for removing DNA molecules containing one or more base pair mismatches in a population of DNA duplexes that have been produced by enzymatic amplification, potentially containing one or more base pair mismatches. The method comprises the steps of contacting the population of DNA duplexes with components of a mismatch repair system under conditions such that an endonucleolytic incision is made on a newly synthesized strand of a DNA duplex molecule containing a base pair mismatch so that such a molecule cannot produce a full-sized product in a subsequent round of enzymatic amplification.

By "endonucleolytic cleavage" is meant cleavage on the unmethylated strand at a hemimethylate of GATC sequence by components of a mismatch repair system.

By "full sized product" is meant a molecule that includes the entire region of interest that is subject to amplification. Molecules that contain endonucleolytic cleavage cannot be amplified in subsequent rounds to produce full sized product and thus will be eliminated from the final amplified product population.

In a preferred embodiment the mismatch repair system is the methyl-directed mismatch repair system of E. coli and the components are Muts, MutL, and MutH proteins, and ATP.

Methods to remove from a population molecules containing a base pair mismatch

In a further embodiment the invention features a method for removing DNA duplex molecules containing base pair mismatches in a population of heteroduplex DNA molecules produced from different sources. The method comprises contacting the population of DNA duplex molecules potentially containing base pair mismatches with some or all components of a mismatch repair system under conditions such that the component or components form a complex with the DNA having a base pair mismatch, and not with a DNA duplex lacking a base pair mismatch, and removing DNA molecules containing the complex or the product of the complex.

By "product of the complex" is meant a DNA duplex that has incorporated biotinylated nucleotides.

By "some or all components of a mismatch repair system" is meant either a complete mismatch repair system such that the complete reaction is carried out or only the proteins of the system which specifically bind to the mismatch.

In preferred embodiments the mismatch repair system is the methyl-directed mismatch repair system of E. coli; some or all protein of the mismatch repair system have been affixed to a solid support and removal by adsortion; the complex interacts with other cellular proteins, and removal of the complex occurs through the interaction; and the conditions include the use of biotinylated nucleotides such that the nucleotides are incorporated into duplex molecules that contained a base pair mismatch and such duplexes are removed by binding to avidin.

By "some or all proteins" is meant, for example, E. coli proteins MutS, MutL, and MutH.

By "attached to a solid support" is meant a means, such as by fusion with glutathione transferase, by which a protein is attached to a solid support system and still remains functional.

By "adsortion" is meant specific binding to some or all of the proteins of the mismatch repair system affixed to a solid support so that separation from other molecules that do not bind to the solid support affixed proteins occurs.

By "interacts with other cellular proteins" is meant interaction between mismatch repair system protein or between those proteins and other proteins. For example, the interaction of MutS bound to a duplex DNA containing a mismatch with MutL or RecA.

Kits containing a mismatch repair system

In a preferred embodiment, a kit for correcting base pair matches in duplex DNA molecules including one or more of the following components comprising the following purified components: an aliquot of E. coli MutH, MutL, and MutS proteins or species variations thereof, an aliquot of DNA helicase II, an aliquot of single-strand DNA binding protein, an aliquot of DNA polymerase III holoenzyme, an aliquot of exonuclease I, an aliquot of Exo VII or RecJ, an aliquot of DNA ligase, an aliquot of ATP, and an aliquot of four deoxynucleoside triphosphates.

A further embodiment of this aspect of this invention includes an assay kit for eliminating DNA molecules containing one or more base pairing mismatches from a population of heterohybrid duplex molecules formed by base pairing of single-stranded DNA molecules obtained from a first and a second source comprising one or more of the following components, an aliquot of proteins of a mismatch repair system, and an aliquot of a recombinase protein.

By "proteins of a mismatch repair system" are meant proteins that modulate the activity of a recombinase protein.

In a preferred embodiment, the proteins of the mismatch correction system are the MutS and MutL proteins of E. coli.

Another aspect of the invention features an assay kit for removing DNA molecules containing one or more base pair mismatches comprising an aliquot of one or more proteins of a mismatch repair system that have been affixed to a column support.

In a preferred embodiment, the protein of the mismatch repair system is the MutS protein of E. coli.

Another aspect of the invention features a kit for fractionating a heteroduplex DNA population into two pools, one of which was mismatch-free at the beginning of the procedure, the second of which represents duplexes that contained mispaired bases at the beginning of the procedure. This kit is comprised of one or more of the following components: an aliquot of all components of complete mismatch repair system; an aliquot of biotinylated nucleotides; and an aliquot of avidin or an avidin-based support.

In a preferred embodiment, the mismatch repair system is from E. coli and consists of products of the mutH, mutL, and mutS genes, DNA helicase II, single-strand DNA binding protein, DNA polymerase III holoenzyme, exonuclease I, exonuclease VII or RecJ exonuclease, DNA ligase, and ATP.

The following Examples are provided for further illustrating various aspects and embodiments of the present invention and are in no way intended to be limiting of the scope.

EXAMPLE 1

DNA Mismatch Correction in a Defined System

In order to address the biochemistry of methyl-directed mismatch correction, the reaction has been assayed in vitro using the type of substrate illustrated in FIG. 1. Application of this method to cell-free extracts of E. coli (A. L. Lu, S. Clark, P. Modrich, Proc. Natl. Acad. Sci. USA 80, 4639, 1983) confirmed in vivo findings that methyl-directed repair requires the products of four mutator genes, mutH, mutL, mutS and uvrD (also called mutU), and also demonstrated a requirement for the E. coli single-strand DNA binding protein (SSB). The dependence of in vitro correction on mutH, mutL and mutS gene products has permitted isolation of these proteins in near homogeneous, biologically active forms. The MutS protein binds to mismatched DNA base pairs; the MutL protein binds to the MutS-heteroduplex complex (M. Grilley, K. M. Welsh, S.-S. Su, P. Modrich, J. Biol. Chem. 264, 1000, 1989); and the 25-kD MutH protein possesses a latent endonuclease that incises the unmethylated strand of a hemimethylated d(GATC) site (K. M. Welsh, A.-L. Lu, S. Clark, P. Modrich, J. Biol. Chem. 262, 15624, 1987), with activation of this activity depending on interaction of MutS and MutL with a heteroduplex in the presence of ATP (P. Modrich, J. Biol. Chem. 264, 6597, 1989). However, these three Mut proteins together with SSB and the DNA helicase II product of the uvrD (mutU) gene (I. D. Hickson, H. M. Arthur, D. Bramhill, P. T. Emmerson, Mol. Gen. Genet. 190, 265, 1983) are not sufficient to mediate methyl-directed repair. Below is described identification of the remaining required components and reconstitution of the reaction in a defined system.

Protein and cofactor requirements for mismatch correction. Methyl-directed mismatch correction occurs by an excision repair reaction in which as much as several kilobases of the unmethylated DNA strand is excised and resynthesized (A.-L. Lin, K. Welsh, S. Clark, S.-S. Su, P. Modrich, Cold Spring Harbor Symp. Quant. Biol. 49, 589, 1984). DNA polymerase I, an enzyme that functions in a number of DNA repair pathways, does not contribute in a major way to methyl-directed correction since extracts from a polA deletion strain exhibit normal levels of activity. However extracts derived from a dnaZ$^{ts}$ strain are temperature sensitive for methyl-directed repair in vitro (Table 1).

TABLE 1

Requirement for t and g Subunits of DNA Polymerase III Holoenzyme in Mismatch Repair

| Extract genotype | DNA Pol III addition (ng) | Mismatch Correction Activity (fmol/h/mg) Extract preincubation | | ratio (42°/34°) |
| --- | --- | --- | --- | --- |
| | | 42° | 34° | |
| dnaZ$^{ts}$ | — | 8 | 91 | 0.09 |
| | 57 ng | 75 | 160 | 0.47 |
| dnaZ$^+$ | — | 150 | 160 | 0.94 |
| | 57 ng | 160 | 160 | 1.0 |

Extracts from strains AX727 (lac thi str$^R$ dnaZ20-16) and AX729 (as AX727 except purE dnaZ$^+$) were prepared as described (A.-L. Lin, S. Clark, P. Modrich, Proc. Natl. Acad. Sci. USA 80, 4639, 1983). Samples (110 µg of protein) were mixed with 0.8 µl of 1M KCl and water to yield a volume of 7.2 µl, and preincubated at 42° or 34° C. for 2.5 minutes. All heated samples were then placed at 34° C. and supplemented with 2.2 µl of a solution containing 0.1 µg (24 fmol) of hemimethylated G-T heteroduplex DNA, 16 ng of MutL protein, 50 ng of MutS protein, and buffer and nucleotide components of the mismatch correction assay (A.-L. Lu, S. Clark, P. Modrich, Proc. Natl. Acad. Sci. USA 80, 4639, 1983). DNA polymerase III holoenzyme (57 ng in 0.6 µl) or enzyme buffer was then added, and incubation at 34° C. was continued for 60 min. Heated extracts were supplemented with purified MutL and MutS proteins because these components are labile at 42° C. Activity measurements reflect the correction of heteroduplex sites.

The dnaZ gene encodes the τ and γ subunits of DNA polymerase III holoenzyme (M. Kodaira, S. B. Biswas, A. Kornberg, *Mol. Gen. Genet.* 192, 80, 1983; D. A. Mullin, C. L. Woldringh, J. M. Henson, J. R. Walker, *Mol. Gen. Genet.* 192, 73, 1983), and mismatch correction activity is largely restored to heated extracts of the temperature-sensitive mutant strain by addition of purified polymerase III holoenzyme. Since DNA polymerase III holoenzyme is highly processive, incorporating thousands of nucleotides per DNA binding event, the involvement of this activity is consistent with the large repair tracts associated with the methyl-directed reaction.

Additional data indicate that purified MutH, MutL, and MutS proteins, DNA helicase II, SSB, and DNA polymerase III holoenzyme support methyl-directed mismatch correction, but this reaction is inhibited by DNA ligase, an enzyme that is shown below to be required to restore covalent continuity to the repaired strand. This observation led to isolation of a 55-kD stimulatory protein that obviates ligase inhibition. The molecular weight and N-terminal sequence of this protein indicated identity to exonuclease I (G. J. Phillips and S. R. Kushner, *J. Biol. Chem.* 262, 455, 1987), and homogeneous exonuclease I readily substitutes for the 55-kD stimulatory activity (Table 2). Thus, exonuclease I and the six activities mentioned above mediate efficient methyl-directed mismatch correction in the presence of ligase to yield product molecules in which both DNA strands are covalently continuous.

TABLE 2

Stimulation of in vitro Methyl-Directed Correction by Exonuclease I.

| Protein added | Mismatch correction (fmol/20 min) |
| --- | --- |
| None | 1 |
| 55-kD protein | 18 |
| Exonuclease I | 18 |

Reactions (10 μl) contained 0.05M HEPES (potassium salt, pH 8.0), 0.02M KCl, 6 mM $MgCl_2$, bovine serum albumin (0.05 mg/ml), 1 mM dithiothreitol, 2 mM ATP, 100 μM (each) DATP, dCTP, dGTP, and dTTP, 25 μM β-$NAD^+$, 0.1 μg of hemimethylated, covalently closed G-T heteroduplex DNA (FIG. 1, methylation on c strand, 24 fmol), 0.26 ng of MutH (K. M. Welsh, A.-L. Lin, S. Clark, P. Modrich, *J. Biol. Chem.* 262, 15624, 1987), 17 ng of MutL (M. Grilley, K. R. Welsh, S.-S. Su, P. Modrich, *J. Biol. Chem.* 264, 1000, 1989), 35 ng of MutS (S.-S. Sin and P. Modrich, *Proc. Nat'l Acad. Sci. USA* 83, 5057, 1986), 200 ng of SSB (T. R. Lohman, J. R. Green, R. S. Beyer, *Biochemistry* 25, 21, 1986; U. S. Biochemical Corp.), 10 ng of DNA helicase II (K. Kumura and M. Sekiguchi, *J. Biol. Chem.* 259, 1560, 1984), 20 mg of *E. coli* DNA ligase (U.S. Biochemical Corp.), 95 ng of DNA polymerase III holoenzyme (C. McHenry and A. Kornberg, *J. Biol. Chem.* 252, 6478, 1977), and 1 ng of 55-kD protein or exonuclease I (U.S. Biochemical Corp.) as indicated. Reactions were incubated at 37° C. for 20 minutes, quenched at 55° C. for 10 minutes, chilled on ice, and then digested with Xho I or Hind III endonuclease to monitor correction. Repair of the G-T mismatch yielded a only the G-C containing, Xho I-sensitive product.

The requirements for repair of a covalently closed G-T heteroduplex (FIG. 1) are summarized in Table 3 (Closed circular). No detectable repair was observed in the absence of MutH, MutL, or MutS proteins or in the absence of DNA polymerase III holoenzyme, and omission of SSB or exonuclease I reduced activity by 85 to 90 percent.

TABLE 3

Protein and Cofactor Requirements for Mismatch Correction in a Defined System.

| | Mismatch correction (fmol/20 min) | |
| --- | --- | --- |
| Reaction conditions | Closed Circular Heteroduplex | Open Circular Heteroduplex |
| Complete | 15 | 17 (No MutH, No ligase) |
| minus MutH | <1 | — |
| minus MutL | <1 | <1 |
| minus MutS | <1 | <1 |
| minus DNA polymerase III holoenzyme | <1 | <1 |
| minus SSB | 2 | 1.4 |
| minus exonuclease I | 2 | <1 |
| minus DNA helicase II | 16 | 15 |
| minus helicase II, plus immune serum | <1 | <1 |
| minus helicase II, plus pre-immune serum | 14 | NT |
| minus Ligase/$NAD^+$ | 14 | NT |
| minus $MgCl_2$ | <1 | NT |
| minus ATP | <1 | NT |
| minus dNTP's | <1 | NT |

Reactions utilizing covalently closed G-T heteroduplex (modification on c strand) were performed as described in the legend to Table 2 except that 1.8 ng of exonuclease I was used. Repair of open circular DNA was performed in a similar manner except that RutH, DNA ligase, and β-$NAD^+$ were omitted from all reactions, and the hemimethylated G-T heteroduplex (modification on c strand) had been incised with MutH protein as described in the legend to FIG. 4. When present, rabbit antiserum to helicase II or pre-immune serum (5 μg protein) was incubated at 0° C. for 20 minutes with reaction mixtures lacking $MgCl_2$; the cofactor was then added and the assay was performed as above. Although not shown, antiserum inhibition was reversed by the subsequent addition of more helicase II. With the exception of the DNA polymerase III preparation, which contained about 15% by weight DNA helicase II (text)1 the purity of individual protein fractions was ≧95%. NT not tested.

These findings are in accord with previous conclusions concerning requirements of the methyl-directed reaction. However, in contrast to observations in vivo and in crude extracts indicating a requirement for the uvrD product, the reconstituted reaction proceeded readily in the absence of the added DNA helicase II (Table 2). Nevertheless, the reaction was abolished by antiserum to homogeneous helicase II, suggesting a requirement for this activity and that it might be present as a contaminant in one of the other proteins. Analysis of these preparations for their ability to restore mismatch repair to an extract derived from a uvrD (mutU) mutant and for the physical presence of helicase II by immunoblot assay revealed that the DNA polymerase III holoenzyme preparation contained sufficient helicase II (13 to 15 percent of total protein by weight) to account for the levels of mismatch correction observed in the defined system. Similar results were obtained with holoenzyme preparations obtained from two other laboratories. The purified system therefore requires all the proteins that have been previously implicated in methyl-directed repair.

Figure 2:
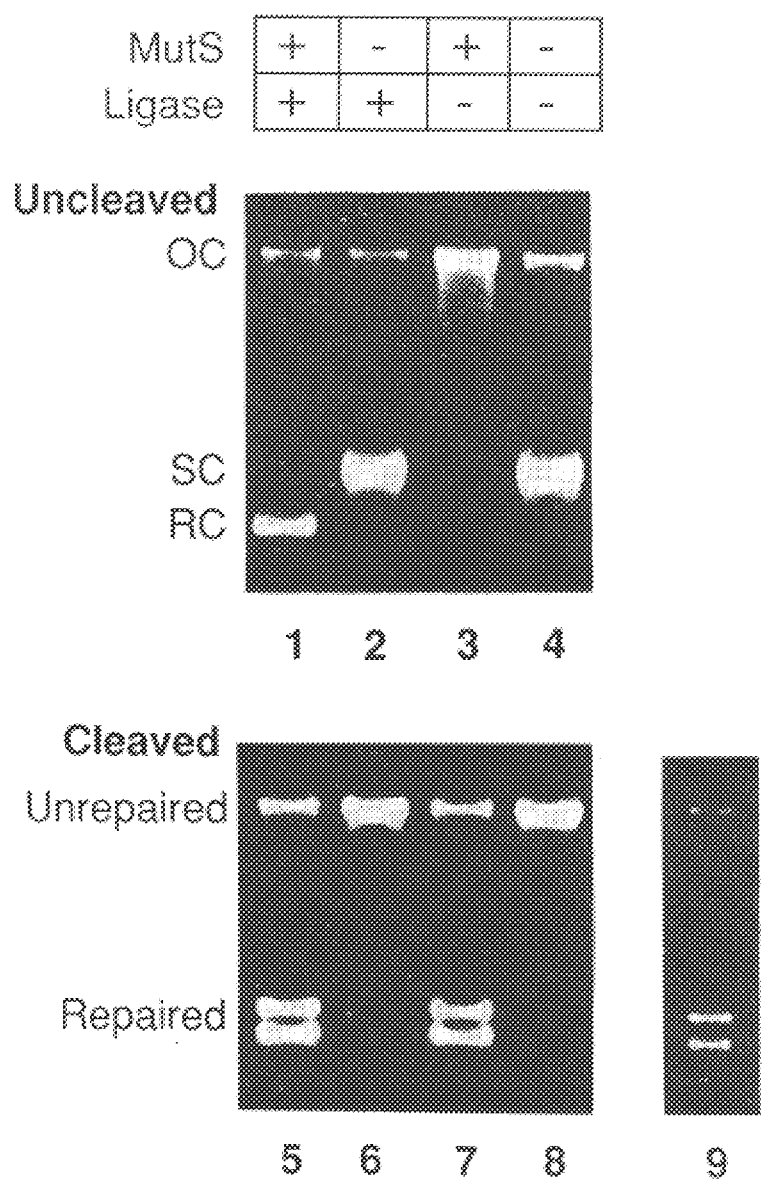
FIG. 2. Requirement for DNA ligase in mismatch correction. Hemimethylated G-T heteroduplex DNA (FIG. 1, 0.6 $\mu$g, d(GATC) methylation on the complementary DNA strand] was subjected to mismatch repair under reconstituted conditions in a 60 $\mu$l reaction (Table 3, closed circular heteroduplex), or in 20 $\mu$l reactions (0.2 $\mu$g of DNA) lacking MutS protein or ligase, or lacking both activities. A portion of each reaction (0.1 $\mu$g of DNA) was treated with EDTA (10 mM final concentration) and subjected to agarose gel electrophoresis in the presence of ethidium bromide (1.5 $\mu$g/ml; top panel, lanes 1–4). Positions are indicated for the unreacted, supercoiled substrate (SC), open circles containing a strand break (OC) and covalently closed, relaxed circular molecules (RC). A second sample of each reaction containing 0.1 $\mu$g of DNA was hydrolyzed with Xho I and Cla I endonucleases (FIG. 1) to score G-T to G-C mismatch correction and subjected to electrophoresis in parallel with the samples described above (bottom panel, lanes 5–8). The remainder of the complete reaction (0.4 $\mu$g DNA, corresponding to the sample analyzed in lane 1) was made 10 mM in EDTA, and subjected to electrophoresis as described above. A gel slice containing closed circular, relaxed molecules was excised and the DNA eluted. This sample was cleaved with Xho I and Cla I and the products analyzed by electrophoresis (lane 9).

The rate of correction of the closed circular heteroduplex was unaffected by omission of DNA ligase (Table 3), but the presence of this activity results in production of a covalently closed product. Incubation of a hemimethylated, supercoiled G-T heteroduplex with all seven proteins required for correction in the presence of DNA ligase resulted in extensive formation of covalently closed, relaxed, circular molecules. Production of the relaxed DNA was dependent on MutS (FIG. 2) and MutL proteins, and the generation of this species was associated with heteroduplex repair (FIG. 2). Correction also occurred in the absence of ligase, but in this case repair products were open circular molecules, the formation of which depended on the presence of MutS (FIG. 2). Since MutS has no known endonuclease activity but does recognize mispairs, it is inferred that open circular molecules are the immediate product of a mismatch-provoked-excision repair process. Ligase closure of the strand break(s) present in this species would yield the covalently closed, relaxed circular product observed with the complete system.

were subject to strand-specific correction, with repair in each case being restricted to the unmodified DNA strand. With a heteroduplex in which neither strand was methylated, some molecules were corrected on one strand, and some were corrected on the other. As can be seen, the hemimethylated heteroduplex bearing methylation on the complementary DNA strand was a better substrate than the alternative configuration in which modification was on the viral strand, with a similar preference for repair of the viral strand being evident with the substrate that was unmethylated on either strand. This set of responses of the purified system to the presence and state of modification of d(GATC) sites reproduce effects previously documented in vivo and in crude extract experiments (R. S. Lahue, S. -S. Su, P. Modrich, Proc. Natl. Acad. Sci. USA 84, 1482, 1987).

TABLE 4

Correction Efficiencies for Different Mismatches.

| Heteroduplex | | | | | Markers | $C^+V^-$ Rate | $C^+V^-$ Bias | $C^+V^-$ Rate | $C^+V^-$ Bias |
|---|---|---|---|---|---|---|---|---|---|
| C | 5'-CTCGA | G | AGCTT | | Xho I | 1.2 | >18 | 0.38 | >5 |
| V | 3'-GAGCT | T | TCGAA | | Hind III | | | | |
| | (SEQ. ID. NO. 1) | | | | | | | | |
| C | 5'0CTCGA | G | AGCTG | | Xho I | 1.1 | >17 | 0.38 | >6 |
| V | 3'-GAGCT | G | TCGAC | | Pvu II | | | | |
| | (SEQ. ID. NO. 2) | | | | | | | | |
| C | 5'-ATCGA | T | AGCTT | | Cla I | 1.0 | >16 | 0.24 | 3 |
| V | 3'-TAGCT | T | TCGAA | | Hind III | | | | |
| | (SEQ. ID. NO. 3) | | | | | | | | |
| C | 5'-ATCGA | A | AGCTT | | Hind III | 0.88 | >20 | 0.20 | >7 |
| V | 3'-TAGCT | A | TCGAA | | Cla I | | | | |
| | (SEQ. ID. NO. 4) | | | | | | | | |
| C | 5'-CTCGA | A | AGCTT | | Hind III | 0.61 | 17 | 0.28 | >5 |
| V | 3'-GAGCT | C | TCGAA | | Xho I | | | | |
| | (SEQ. ID. NO. 5) | | | | | | | | |
| C | 5'-GTCGA | C | AGCTT | | Sal I | 0.60 | 12 | 0.23 | >4 |
| V | 3'-CAGCT | T | TCGAA | | Hind III | | | | |
| | (SEQ. ID. NO. 6) | | | | | | | | |
| C | 5'-GTCGA | A | AGCTT | | Hind III | 0.44 | >13 | 0.21 | 5 |
| V | 3'-CAGCT | T | TCGAA | | Sal I | | | | |
| | (SEQ. ID. NO. 7) | | | | | | | | |
| C | 5'-CTCGA | C | AGCTG | | Pvu II | 0.04 | NS | <0.04 | NS |
| V | 3'-GAGCT | C | TCGAC | | Xho I | | | | |
| | (SEQ. ID. NO. 8) | | | | | | | | |

The set of purified activities identified here as being important in methyl-directed repair support efficient correction. In the experiments summarized in Table 3, the individual proteins were used at the concentrations estimated to be present in the standard crude extract assay for correction as calculated from known specific activity determinations. Under such conditions the rate and extent of mismatch repair in the purified system are essentially identical to those observed in cell-free extracts.

Figure 3:
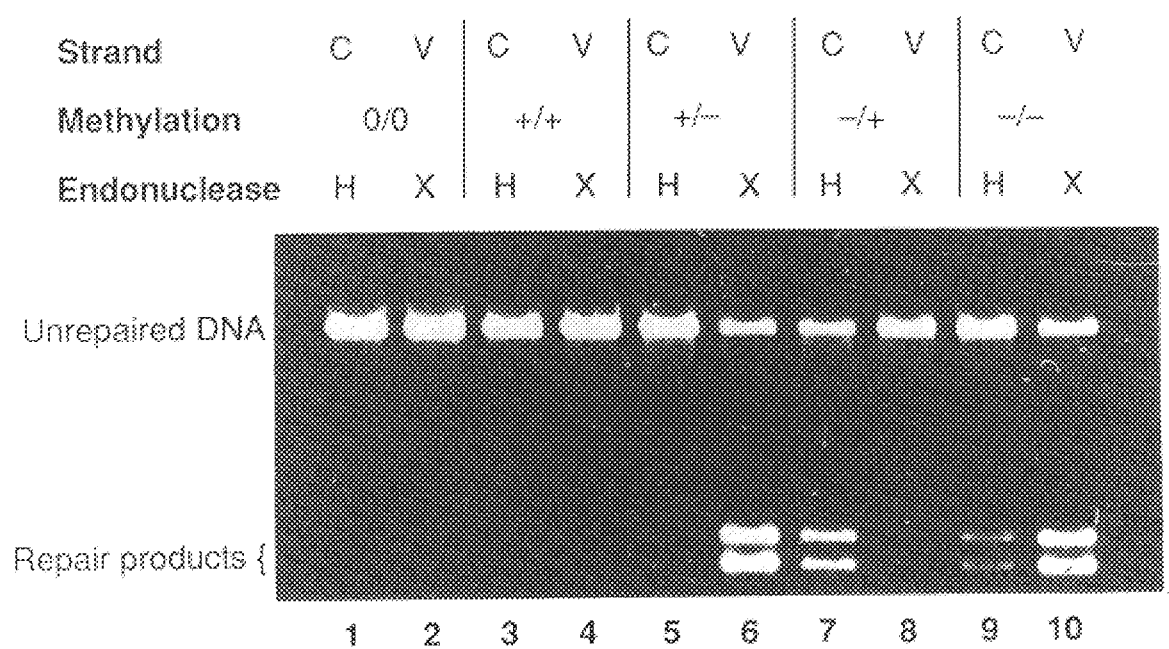
FIG. 3. Methyl-direction of mismatch correction in the purified system. Repair reactions with the G-T heteroduplex (FIG. 1) were performed as described in Table 3 (closed circular heteroduplex) except that reaction volumes were 20 $\mu$l (0.2 $\mu$g of DNA) and the incubation period was 60 minutes. The reactions were heated to 55° for 10 minutes and each was divided into two portions to test strand specificity of repair. G-T to A-T mismatch correction, in which repair occurred on the complementary (c) DNA strand, was scored by cleavage with Hind III and Cla I endonucleases, while hydrolysis with Xho I and Cla I were used to detect G-T to G-C repair occurring on the viral (v) strand. Apart from the samples shown in the left two lanes, all heteroduplexes were identical except for the state of methylation of the single d(GATC) sequence at position 216 (FIG. 1). The state of modification of the two DNA strands at this site is indicated by + and − notation. The G-T heteroduplex used in the experiment shown in the left two lanes (designated 0/0) contains the sequence d(GATT) instead of d(GATC) at position 216, but is otherwise identical in sequence to the other substrates.

DNA sites involved in repair by the purified system. The single d(GATC) sequence within the G-T heteroduplex shown in FIG. 1 is located 1024 base pairs from the mispair. Despite the distance separating these two sites, correction of the mismatch by the purified system responded to the state of modification of the d(GATC) sequence as well as its presence within the heteroduplex (FIG. 3). A substrate bearing d(GATC) methylation on both DNA strands did not support mismatch repair nor did a related heteroduplex in which the d(GATC) sequence was replaced by d (GATT). However, each of the two hemimethylated heteroduplexes Table 4. (Continued) Correction of the eight possible base-base mispairs was tested with the set of covalently closed heteroduplexes described previously including the G-T substrate shown in FIG. 1. With the exception of the mispair and the variations shown at the fifth position on either side, all heteroduplexes were identical in sequence. Each DNA was tested in both hemimethylated configurations under complete reaction conditions (Table 3, closed circular heteroduplex) except that samples were removed at 5-minute intervals over a 20 minute period in order to obtain initial rates (fmol/min). c and v refer to complementary and viral DNA strands, and Bias indicates the relative efficiency of mismatch repair occurring on the two DNA strands (ratio of unmethylated to methylated) as determined 60 minutes after the reaction was started. NS—not significant. With the exception of the C-C heteroduplexes, repair in the absence of MutS protein was less than 20% (in most cases <10%) of that observed in its presence (not shown).

The efficiency of repair by the methyl-directed pathway depends not only on the nature of the mispair, but also on the sequence environment in which the mismatch is embedded (P. Modrich, Ann. Rev. Biochem. 56, 435, 1987). To assess the mismatch specificity of the purified system under conditions where sequence effects are minimized, a set of heteroduplexes were used in which the location and immediate sequence environment of each mispair are essentially identical (S. -S. Su, R. S. Lahue, K. G. Au, P. Modrich, *J. Biol. Chem.* 263, 6829, 1988). This analysis (Table 4) showed that the purified system is able to recognize and repair in a methyl-directed manner seven of the eight possible base-base mismatches, with C-C being the only mispair that was not subject to significant correction. Table 3 also shows that the seven corrected mismatches were not repaired with equal efficiency and that in the case of each heteroduplex, the hemimethylated configuration modified on the complementary DNA strand was a better substrate than the other configuration in which the methyl group was on the viral strand. These findings are in good agreement with patterns of repair observed with this set of heteroduplexes in *E. coli* extracts (Although the patterns of substrate activity observed in extracts and in the purified system are qualitatively identical, the magnitude of variation observed differs for the two systems. Hemimethylated heteroduplexes modified on the complementary DNA strand are better substrates in both systems, but in extracts such molecules are repaired at about twice the rate of molecules methylated on the viral strand. In the purified system these relative rates differ by factors of 2 to 4. A similar effect may also exist with respect to mismatch preference within a given hemimethylated family. Although neither system repairs C-C, the rates of repair of other mismatches vary by a factors of 1.5 to 2 in extracts but by factors of 2 to 3 in the defined system.).

Strand-specific repair directed by a DNA strand break. Early experiments on methyl-directed repair in *E. coli* extracts led to the proposal that the strand-specificity of the reaction resulted from endonucleolytic incision of an unmethylated DNA strand at a d(GATC) sequence. This idea was supported by the finding that purified MutH protein has an associated, but extremely weak d(GATC) endonuclease that is activated in a mismatch-dependent manner in a reaction requiring MutL, MutS, and ATP. The purified system has been used to explore this effect more completely.

Figure 4:
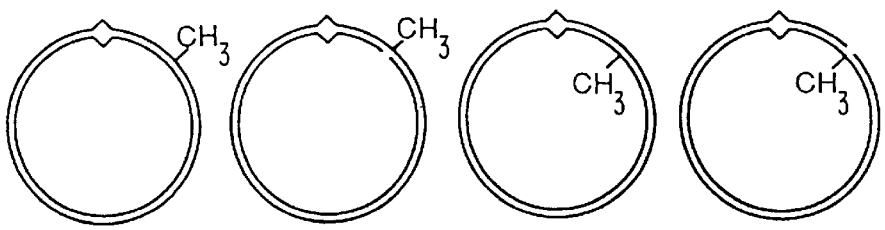
FIG. 4. Strand-specific repair of heteroduplexes containing a single strand scission in the absence of MutH protein. Hemimethylated G-T heteroduplex DNAs (FIG. 1, 5 $\mu$g) bearing d(GATC) modification on the viral or complementary strand were subjected to site-specific cleavage with near homogeneous MutH protein. Because the MutH-associated endonuclease is extremely weak in the absence of other mismatch repair proteins, cleavage at d(GATC) sites by the purified protein requires a MutH concentration 80 times that used in reconstitution reactions. After removal of MutH by phenol extraction, DNA was ethanol precipitated, collected by centrifugation, dried under vacuum, and resuspended in 10 mM Tris-HCl (pH 7.6), 1 mM EDTA. Mismatch correction of MutH-incised and covalently closed, control heteroduplexes was performed as described in the legend to Table 2 except that ligase and NAD$^+$ were omitted. Outside and inside strands of the heteroduplexes depicted here correspond to complementary and viral strands respectively. Values in parentheses indicate repair occurring on the methylated, continuous DNA strand. The absence of MutH protein in preparations of incised heteroduplexes was confirmed in two ways. Preparations of incised molecules were subject to closure by DNA ligase (>80%) demonstrating that MutH protein does not remain tightly bound to incised d(GATC) sites. Further, control experiments in which each MutH-incised heteroduplex was mixed with a closed circular substrate showed that only the open circular form was repaired if MutH protein was omitted from the reaction whereas both substrates were corrected if MutH protein was present (data not shown).

The two hemimethylated forms of the G-T heteroduplex shown in FIG. 1 were incised using high concentrations of purified MutH protein to cleave the unmethylated DNA strand at the d(GATC) sequence (➤pGpApTpC). After removal of the protein, these open circular heteroduplexes were tested as substrates for the purified system in the absence of DNA ligase. Both open circular species were corrected in a strand-specific manner and at rates similar to those for the corresponding covalently closed heteroduplexes (FIG. 4). As observed with closed circular heteroduplexes, repair of the MutH-cleaved molecules required MutL, MutS, SSB, DNA polymerase III holoenzyme, and DNA helicase II (FIG. 4 and open circle entries of Table 2), but in contrast to the behavior of the closed circular substrates, repair of the mismatch within the open circular molecules occurred readily in the absence of MutH protein. Thus prior incision of the unmethylated strand of a d(GATC) site can bypass the requirement for MutH protein in strand-specific mismatch correction.

Figure 5:
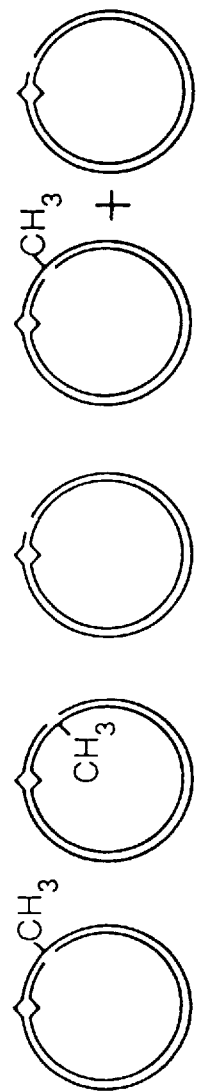
FIG. 5. Requirements for MutH protein and a d(GATC) sequence for correction in the presence of DNA ligase. Hemimethylated G-T heteroduplexes incised on the unmethylated strand at the d(GATC) sequence were prepared as described above in FIG. 4. A G-T heteroduplex devoid of d(GATC) sites (FIG. 4) and containing a single-strand break within the complementary DNA strand at the Hinc II site (position 1) was constructed as described previously (Lahue et al. supra). Mismatch correction assays were performed as described in Table 3, with ligase (20 ng in the presence of 25 $\mu$M NAD$^+$) and MutH protein (0.26 ng) present as indicated. Table entries correspond to correction occurring on the incised DNA strand, with parenthetic values indicating the extent of repair on the continuous strand. Although not shown, repair of the nicked molecule lacking a d(GATC) sequence (first entry of column 3) was reduced more than an order of magnitude upon omission of MutL, MutS, SSB or DNA polymerase III holoenzyme.

The nature of the MutH-independent repair was examined further to assess the effect of ligase on the reaction and to determine whether a strand break at a sequence other than d(GATC) can direct correction in the absence of MutH protein (FIG. 5). As mentioned above, a covalently closed G-T heteroduplex that lacks a d(GATC) sequence is not subject to repair by the purified system in the presence (FIG. 3) or absence of DNA ligase. However, the presence of one strand-specific, site-specific break is sufficient to render this heteroduplex a substrate for the purified system in the absence of ligase and RutH protein (FIG. 5). Repair of this open circular heteroduplex was limited to the incised, complementary DNA strand, required presence of MutL and MutS proteins, DNA polymerase III, and SSB, and correction of the molecule was as efficient as that observed with the hemimethylated heteroduplex that had been cleaved by MutH at the d(GATC) sequence within the complementary strand. Although the presence of a strand break is sufficient to permit strand-specific correction of a heteroduplex in the absence of MutH and ligase, the presence of the latter activity inhibited repair not only on the heteroduplex lacking a d(GATC) sequence but also on both hemimethylated molecules that had been previously incised with MutH protein (FIG. 5). This inhibition by ligase was circumvented by the presence of MutH protein, but only if the substrate contained a d(GATC) sequence, with this effect being demonstrable when both types of heteroduplex were present in the same reaction (FIG. 5, last column). This finding proves that MutH protein recognizes d(GATC) sites and is consistent with the view that the function of this protein in mismatch correction is the incision of the unmethylated strand at this sequence.

EXAMPLE 2

Purification of MutY Protein

Purification of MutY Protein *E. coli* RK1517 was grown at 37° C. in 170 liters of L broth containing 2.5 mM $KH_2PO_4$, 7.5 mM $Na_2HPO_4$ (culture pH=7.4) and 1% glucose. The culture was grown to an $A_{590}$ of 4, chilled to 10° C. and cells were harvested by continuous flow centrifugation. Cell paste was stored at 70° C. A summary of the MutY purification is presented in Table 1. Fractionation procedures were performed at 0°–4° C., centrifugation was at 13,000× g, and glycerol concentrations are expressed as volume percent.

Frozen cell paste (290 g) was thawed at 4° C., resuspended in 900 ml of 0.05M Tris-HCl (pH 7.5), 0.1M NaCl, 1 mM dithiothreitol, 0.1 mM EDTA, and cells were disrupted by sonication. After clarification by centrifugation for 1 hr, the lysate (Fraction I, 970 ml) was treated with 185 ml of 25% streptomycin sulfate (wt/vol in 0.05M Tris-HCl (pH 7.5), 0.1M NaCl, 1 mM dithiothreitol, 0.1 mM EDTA) which was added slowly with stirring. After 30 min of additional stirring, the solution was centrifuged for 1 h, and the supernatant (1120 ml) was treated with 252 g of solid ammonium sulfate which was added slowly with stirring. After 30 min. of additional stirring, the precipitate was collected by centrifugation for 1 h, resuspended to a final volume of 41 ml in 0.02M potassium phosphate (pH 7.5), 0.1 mM EDTA, 10% (vol/vol) glycerol, 1 mM dithiothreitol, and dialyzed against two 2 1 portions of 0.02 M potassium phosphate (pH 7.5), 0.1M KCl, 0.1 mM EDTA, 1 mM dithiothreitol, 10% glycerol (2 h per change). The dialyzed material was clarified by centrifugation for 10 min to yield Fraction II (45 ml).

Fraction II was diluted 10-fold into 0.02M potassium phosphate (pH 7.5), 0.1M EDTA, 1 mM dithiothreitol, 10% glycerol so that the conductivity of the diluted solution was comparable to that of the dilution buffer containing 0.1M KCl. The solution was performed on small aliquots of Fraction II, and diluted samples were immediately loaded at 1 ml/min onto a 14.7 cm×12.6 $cm^2$ phosphocellulose column equilibrated with 0.02M potassium phosphate (pH 7.5), 0.1M KCl, 0.1 mM EDTA, 1 mM dithiothreitol, 10% glycerol. The column was washed with 400 ml of equilibration buffer, and developed with a 2 liter linear gradient of KCl (0.1 to 1.0M) in 0.02M potassium phosphate (pH 7.5), 0.1 mM EDTA, 1 mM dithiothreitol, 10% glycerol. Fractions containing MutY activity, which eluted at about 0.4M KCl, were pooled (Fraction III, 169 ml).

Fraction III was dialyzed against two 500 ml portions of 5 mM potassium phosphate (pH 7.5), 0.05M KCl, 0.1 mM EDTA, 1 mM dithiothreitol, 10% glycerol (2 h per change) until the conductivity was comparable to that of the dialysis buffer. After clarification by centrifugation at for 10 min, the solution was loaded at 0.5 ml/min onto a 21 cm×2.84 cm$^2$ hydroxylapatite column equilibrated with 5 mM potassium phosphate, pH 7.5, 0.05M KCl, 0.1 mM EDTA, 1 mM dithiothreitol, 10% glycerol. After washing with 130 ml of equilibration buffer, the column was eluted with a 600 ml linear gradient of potassium phosphate (5 mM to 0.4M, pH 7.5) containing 0.05M KCl, 1 mM dithiothreitol, 10% glycerol. Fractions eluting from the column were supplemented with EDTA to 0.1 mM. Peak fractions containing 60% of the total recovered activity, which eluted at about 0.1M potassium phosphate, were pooled (Fraction IV, 24 ml). The remaining side fractions contained impurities which could not be resolved from MutY by MonoS chromatography.

Fraction IV was diluted by addition of an equal volume of 0.1 mM EDTA, 1 dithiothreitol, 10% glycerol. After clarification by centrifugation for 15 min, diluted Fraction IV was loaded at 0.75 ml/min onto a Pharmacia HR 5/5 MonoS FPLC column that was equilibrated with 0.05M sodium phosphate (pH 7.5), 0.1M NaCl, 0.1 mM EDTA, 0.5 mM dithiothreitol, 10% glycerol. The column was washed at 0.5 ml/min with 17 ml of equilibration buffer and developed at 05 ml/min with a 20 ml linear gradient of NaCl (0.1 to 0.4M) in 0.05M sodium phosphate (pH 7.5), 0.1 mM EDTA, 0.5 mM dithiothreitol, 10% glycerol. Fractions with MutY activity, which eluted at approximately 0.2M NaCl, were pooled (Fraction V, 2.6 ml). Fraction V was divided into small aliquots and stored at −70° C.

TABLE 5

Purification of MutY protein from 290 g of E. coli RK1517

| Fraction | Step | Total Protein mg | Specific Activity units/mg | Yield Percent |
|---|---|---|---|---|
| I | Extract | 10,900 | 40 | (100) |
| II | Ammonium sulfate | 1,350 | 272 | 84 |
| III | Phosphocellulose | 66 | 10,800 | 160 |
| IV | Hydroxylapatite | 1.4 | 136,000 | 44 |
| V | MonoS | 0.16 | 480,000 | 18 |

Specific A•G to C-G mismatch correction in cell-free extracts was determined as described previously (Au et al. 1988), except that ATP and glutathione were omitted from the reaction and incubation was for 30 min instead of 1 h. For complementation assays, each 0.01 ml reaction contained RK1517-Y33 extract (mutS mutY) at a concentration of 10 mg/ml protein. One unit of MutY activity is defined as the amount required to convert 1 fmol of A•G mismatch to C-G base pair per h under complementation conditions.

Assay for MutY-dependent, A•G-specific glycosylase

DNA restriction fragments were labeled at either the 3' or 5' ends with $^{32}$P, Glycosylase activity was then determined in 0.01 ml reactions containing 10 ng end-labeled DNA fragments, 0.02M Tris-HCl, pH 7.6, 1 mM EDTA, 0.05 mg/ml bovine serum albumin, and 2.7 ng MutY. After incubation at 37° C. for 30 min, the reaction mixture was treated with 2.5×10$^{-3}$ units of HeLa AP endonuclease II in the presence of 11 mM MgCl$_2$ and 0.005% Triton X-100 for 10 min at 37° C. Reactions were quenched by the addition of an equal volume of 80% formamide, 0.025% xylene cyanol, 0.025% bromphenol blue, heated to 80° C. for 2 min, and the products analyzed on an 8% sequencing gel. Control reactions contained either no MutY, no A•G mismatch or no AP endonuclease II.

Strand cleavage at the AP site generated by MutY could also be accomplished by treatment with piperidine instead of treatment with AP endonuclease II. After incubation for 30 min. at 37° C. with MutY as described above, the reaction mixture was precipitated with ethanol in the presence of carrier tRNA, then resuspended in 1M piperidine and heated at 90° C. for 30 min. After two additional ethanol precipitations, changing tubes each time, the pellet was resuspended in a minimum volume of water to which was added an equal volume of 80% formamide, 0.025% xylene cyanol, 0.025% bromphenol blue. The products were then analyzed on an 8% sequencing gel.

EXAMPLE 3

Genetic Mapping Point Mutations in the Human Genome

The full novelty and utility of the present invention may be further appreciated by reference to the following brief description of selected specific embodiments which advantageously employ various preferred forms of the invention as applied to a common problem in genetic mapping of point mutations in the human genome. In the course of constructing gene linkage maps, for example, it is frequently desirable to compare the sequence of a cloned DNA fragment with homologous sequences in DNA extracted from a human tissue sample. Substantially all base pairs in the entire homologous sequence of the cloned DNA fragment are compared to those of the human tissue DNA, most advantageously in a single test according to the present invention, merely by contacting both strands of the human tissue DNA molecule with both radiolabeled complementary strands of the second DNA molecule under conditions such that base pairing occurs, contacting the resulting DNA duplexes with the E. coli MutS protein that recognizes substantially all base pair mismatches under conditions such that the protein forms specific complexes with its cognate mispairs, and detecting the resulting DNA:protein complexes by contacting the complexes with a membranous nitrocellulose filter under conditions such that protein:DNA complexes are retained while DNA not complexed with protein is not retained, and measuring the amount of DNA in the retained complexes by a standard radiological methods or by utilizing any of the other methods of the invention; e.g., altered electrophoretic mobility, or detection by use of antibodies.

If the above detection test indicates the presence of sequence differences between the human tissue DNA and the cloned DNA and localization is required, or, in the alternative, if such differences are suspected and localization as well as detection of them is desired in a first analysis, the another method of this invention may be applied for these purposes. An embodiment of this aspect of the invention that may be most advantageously employed comprises the steps of contacting both strands of the human tissue DNA molecule with both radiolabeled complementary strands of the second DNA molecule (usually without separation from the cloning vector DNA) under conditions such that base pairing occurs, contacting the resulting DNA duplexes with MutHLS to produce a GATC cleavage reaction or a modified form of MutS protein of *E. coli* to which is attached an hydroxyl radical cleaving function under conditions such that the radical cleaving function cleaves both strands of the DNA within about 20 base pairs of substantially all DNA base mispairs. In the absence of any DNA base mispairs in the DNA duplexes comprising complementary strands of the human tissue and cloned DNAs, no DNA fragments smaller than the cloned DNA (plus vector DNA, if still attached) would be detected. Determination of the location of any double-stranded DNA cleavages by the modified MutS protein to within a few kbp or less of some restriction enzyme cleavage site within the cloned DNA is determined by standard restriction enzyme mapping approaches. If greater precision in localization and identification of a single base difference is desired, sequencing could be confined to those particular fragments of cloned DNA that span at least one base sequence difference localized by this method and are cleaved by a restriction enzyme at the most convenient distance of those sequence differences for direct sequencing.

The examples herein can be changed to make use of other methods of separation to identify mismatches, such as a filter-binding assay, as well as the nicking reaction with MutS and MutL. While large (at least 20 kbp) or small DNA molecules can be used in these methods those of between 1–10 kbp are preferred.

EXAMPLE 4

DNA Mismatch Detection Kit

Kit contains MutS protein, dilution buffer, annealing buffer, reagents to generate complementary and mismatched control duplexes and filter binding protocol. It can be used to detect single-base mismatches in oligonucleotides.

MutS kit components:

MutS protein in storage buffer: 50 mM HEPES pH7.2, 100 mM KCl, 1 mM EDTA, 1 mM DTT;

MutS1: 16mer oligonucleotide GATCCGTCGACCT-GCA (SEQ. ID. NO. 9) (all such oligonucleotides are written 5' to 3' herein) in water (2 μM);

MutS2: 16mer oligonucleotide TGCAGGTCGACG-GATC (SEQ. ID. NO. 10) 1 μM in annealing buffer 1 μM: 20 mM Tris/HCl pH 7.6, 5 mM, MgCl$_2$, 0.1 mM DTT, 0.01 mM EDTA;

MutS3: 16mer oligonucleotide TGCAGGTTGACG-GATC (SEQ. ID. NO. 11) 1 μM in annealing buffer;

Assay buffer/annealing buffer/wash buffer, 20 mM Tris/HCl pH 7.6, 5 mM MgCl$_2$, 0.1 mM DTT, 0.01 mM EDTA;

Protein storage/dilution buffer: 50 mM HEPES pH 7.2, 100 mM KCl, 1 mM EDTA, 1 mM DTT.

The DNA mismatch detection kit contains three 16-mer oligonucleotides labeled MUTS1, MUTS2, and MUTS3 for testing the performance of MutS protein. When MUTS1 and MUTS2 are annealed, a perfectly matched duplex results. When MUTS1 and MUTS3 are annealed, a duplex containing a single G-T mismatch results. These serve as contrtol substrates for MutS binding.

Kinase Labeling of MUTS1 Oligonucleotide

This protocol uses half the amount of oligonucleotide contained in the kit. To a microcentrifuge tube on ice add the following:

| | |
|---|---|
| MUTS1 Oligonucleotide (2 μm) | 15 μl (30 pmoles) |
| 10X T4 Polynucleotide Kinase Buffer | 3 μl |
| $^{32}$P-ATP (3000 Ci/mmole) | 1 μl |
| ATP (10 μM) | 2.5 μl |
| Sterile dH$_2$O | 7.5 μl |
| T4 Polynucleotide Kinase (30 units/μl) | 1 μl (30 units) |

Incubate the reaction mixture for 10 min at 37° C. Then incubate 10 min at 70° C. Spot two independent 1 μl aliquots of the mixture on a SureCheck TLC plate and also spot a dilution of $^{32}$P-ATP (1:30 in water) in a separate lane and run with the elution mixture. Expose the developed plate to X-ray film for 5 min. Scrape all radioactive spots from both experimental lanes of the plate and count them in a liquid scintillation counter to determine the % incorporation of label. This value is typically 40–60%. If a significant labeled ATP spot is present in the kinase reaction lanes on the plate, the labeled oligonucleotide must be purified before use (TLC or gel), since $^{32}$P-ATP will contribute to background in the filter binding assay. In our experience, this is usually not necessary.

Keep in mind that the MUTS1 oligo stock is 2 pmol/μl and that the final concentration should be 1 pmol/μl. It is critical that this final concentration be as exact as possible, since the concentration determines the amount of MUTS1 in the next (annealing) step and hence, the amount of DNA available for binding by the protein.

Annealing Reactions

Two separate reactions are carried out: MUTS1/MUTS2 and MUTS1/MUTS3. In both cases, the $^{32}$P-labeled MUTS1 from Step 1 is used.

| Complementary | | Mismatched | |
|---|---|---|---|
| MUTS1 (kinased) | 14 μl = 14 pmol | MUTS1 (kinased) | 14 μl = 14 pmols |
| MUTS2 (1 μM) | 28 μl = 28 pmol | MUTS3 (1 μM) | 28 μl = 28 pmols |
| annealing buffer | 28 μl | annealing buffer | 28 μl |
| | 70 μl | | 70 μl |

1. Heat each mixture for 10 min at 70° C.
2. Incubate for 30 min at room temperature.
3. Hold on ice until ready to use.

The molar ratio of MUTS2/MUTS1 and MUTS3/MUTS1 is 2:1 in the above reactions and this should be maintained for optimal results. Lowering the ratio of unlabeled to labeled strand may lead to very high background in the filter binding assay, presumably caused by sticking of labeled ssDNA to nitrocellulose.

Assay of MutS Binding by the Gel Shift Method

The binding of MutS to mismatches can be assessed using the technique of Gel Shift Mobility Assay (GSMA), a useful tool to identify protein-DNA interactions which may regulate gene expression. Below is a protocol for performing GSMA on the MUTS1/MUTS3 mismatched duplex contained in the the mismatch detection kit. Optimum conditions may vary depending on the particular mismatch being detected or the length of the oligonucleotide.

All binding reactions should be carried out on ice. The total binding reaction volume is 10 µl. Add 4 µl of a MutS protein dilution (prepared using dilution buffer in the kit) containing 0.5–5 pmols (0.125–1.25 units) of MutS protein (1 pmol=97 ng) to 6 µl=1.2 pmols of $^{32}$P-labeled MUTS1/MUTS3 heteroduplex. Also add comparable amounts of MutS protein to labeled MUTS1/MUTS2 matched duplex to serve as a control. A control incubation consisting only of mismatched heteroduplex (no MutS protein) should also be run. Incubate all reactions on on ice for 30 min.

To 3 µl of the DNA/MutS mixture from each incubation add 1 µl of a 50% w/v sucrose solution.

Load 2 µl of the mixture from Step 2 onto a 6% non-denaturing polyacrylmide gel prepared in Tris-acetate-EDTA (TAE) buffer (Sambrook et al., "Molecular Cloning: A Laboratory Manual, Second Edition, cold Spring Harbor Laboratory, New York (1989)) to which MgCl$_2$ has been added to a final concentration of 1 mM and run the gel at 10 V/cm and 4° C. in TAE buffer containing 1 mM MgCl$_2$ until bromophenol blue dye (loaded into an adjacent well) has migrated approximately half way down the gel. The presence of Mg++ in the gel and running buffer is critical for optimal results in the GSMA assay of MutS protein.

Filter Binding Assay

The total binding reaction volume is 10 µl. It consists of 6 µl, or 1.2 pmoles, of duplex DNA and 4 µl of a MutS protein dilution containing 0.5–5 pmoles (0.125=1.25 units) of MutS protein (1 pmol=97 ng). Each type of duplex, complementary and mismatched, should be assayed in duplicate or triplicate along with a no protein control for each annealing, which will serve as the background to subtract.

In order to use the filter binding assay it will be necessary to make up additional annealing buffer for use in the washing step. Add 20 ml of 1M Tris-HDl, pH 7.6, 5 ml of 1M MgCl$_2$, 0.1 ml of 1M DTT, and 0.02 ml of 0.5M EDTA to distilled water and bring the volume to 1 liter.

For each binding assay, add the following to a 0.5 ml microcentrifuge tube on ice:

MUTS1/MUTS2 (Control) OR

MUTS1/MUTS3 (Mismatched)

Annealing Mixture 6 µl

Set up the filtration apparatus and presoak the nitrocellulose filters in annealing buffer.

Add 4 µl of MutS protein dilution to the annealing mixtures on ice. Also include no protein controls for each annealing.

After 30 minutes, begin filtration of samples. Caution, use a slow rate of filtration. It should take at least a second or two for the 10 µl sample to filter.

Immediately wash the filters with 5 ml each of cold annealing buffer. This should take 20–30 seconds.

Place the filters in liquid scintillation vials, add fluid and count for 2 minutes each.

Determine the input cpm for each annealing as follows: To 6 µl of annealing mixture, add 54 µl of water and count 2–3 aliquots of 6 µl each in scintillation fluid. The input cpm is then 10× the average of the cpm of the dilution.

Determine the cpm/pmole of DNA as follows:

$$\frac{\text{cpm of 6 }\mu\text{l aliquot} \times \text{dilution} \times \text{fraction of label incorporate}}{p\text{mol of DNA in annealing reaction}}$$

A 6 µl annealing contains 1.2 pmoles of DNA
A typical kinase reaction may give 42% incorporation (determined previously)
A 6 µl aliquot of 10× dilution may be 10,600 cpm $$\frac{10,600 \times 10 \times 0.42}{1.2} = 37,100 \text{ cpm}/p\text{mole DNA}$$

Determine the pmoles of DNA bound by various pmoles of MutS. First, determine the pmoles of MutS protein in a binding reaction.:

$$\text{concentration of MutS} \times \text{volume of protein added/molecular weight of MutS} \times \text{culution factor}$$

Example: If 4 µl of a 6× dilution of MutS at 250 µg/ml is used, then:

$$\frac{250 \text{ ng }\mu l \times 4 \mu l}{97 \text{ ng}/p\text{mole} \times 6} = 1.72 \, p\text{moles of }MutS \text{ in reaction}$$

Then, determine the pmoles of DNA bound:

$$\frac{\text{cpm retained on filter with }MutS\text{ protein-cpm on no protein filter}}{\text{cpm}/p\text{mole of DNA}}$$

Example: One gets 15,470 cpm on the filter with MutS and 340 cpm with no protein $$\frac{15,470 \text{ cpm} - 340 \text{ cpm}}{37,100 \text{ cpm}/p\text{mole}} = 0.408 \, p\text{moles of DNA bound}$$

Determine the number of pmoles of MutS required to bind 1 pmole of DNA (i.e., a unit of MutS). In the above example, 1.72 pmoles of MutS bound 0.409 pmoles of DNA, such that one unit 1.72/0.408=4.2 pmoles MutS per mole DNA.

EXAMPLE 5

Effects of MutS and MutL on RecA-catalyzed Strand Transfer

Figure 6:
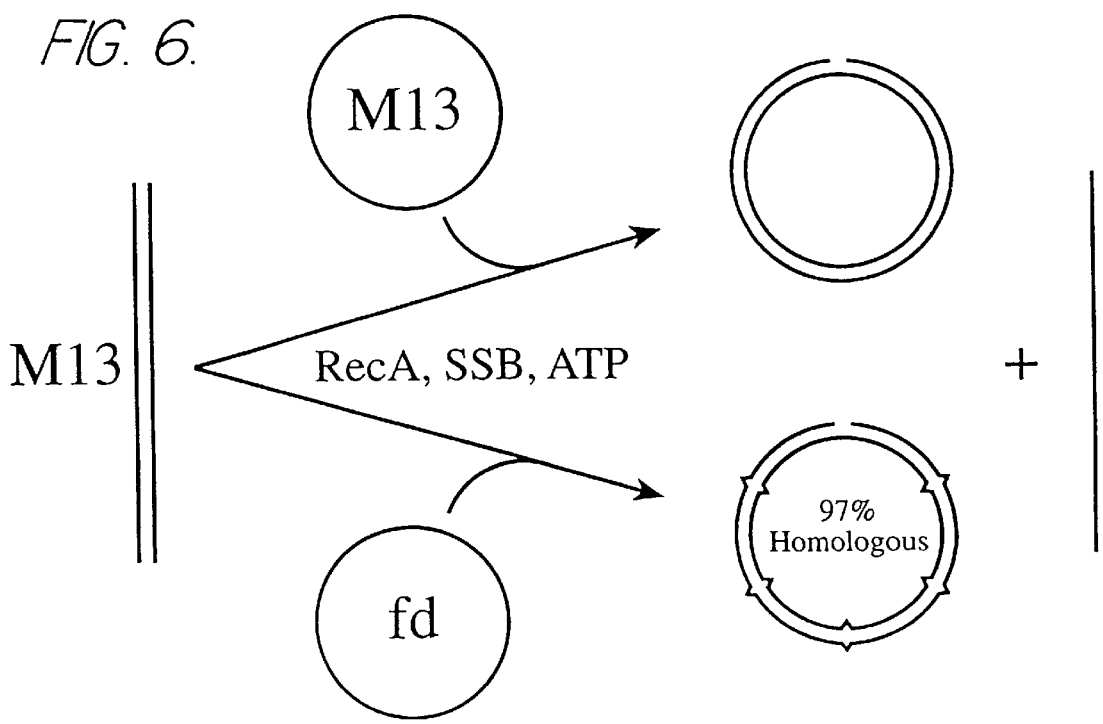
FIG. 6 is a diagrammatic representation of the model system used to evaluate MutS and MutL effects on RecA catalyzed strand transfer.

A model system used to evaluate MutS and MutL effects on RecA catalyzed strand transfer is depicted in FIG. 6. The assay for RecA-catalyzed strand transfer between homologous and quasi-homologous DNA sequences employed the three strand reaction in which one strand from a linear duplex DNA is transferred to an homologous, single-stranded DNA circle (Cox, 78 Proc. Natl. Acad. Sci. USA 3433, 1981. These experiments exploited the previous observation that RecA is able to support strand transfer between related fd and M13 DNAs (Bianchi et al., 35 Cell 511, 1983; DasGupta et al., 79 Proc. Natl. Acad. Sci USA 762, 1982, which are approximately 97% homologous at the nucleotide level. The vast majority of this variation is due to single base pair changes.

Figure 7:
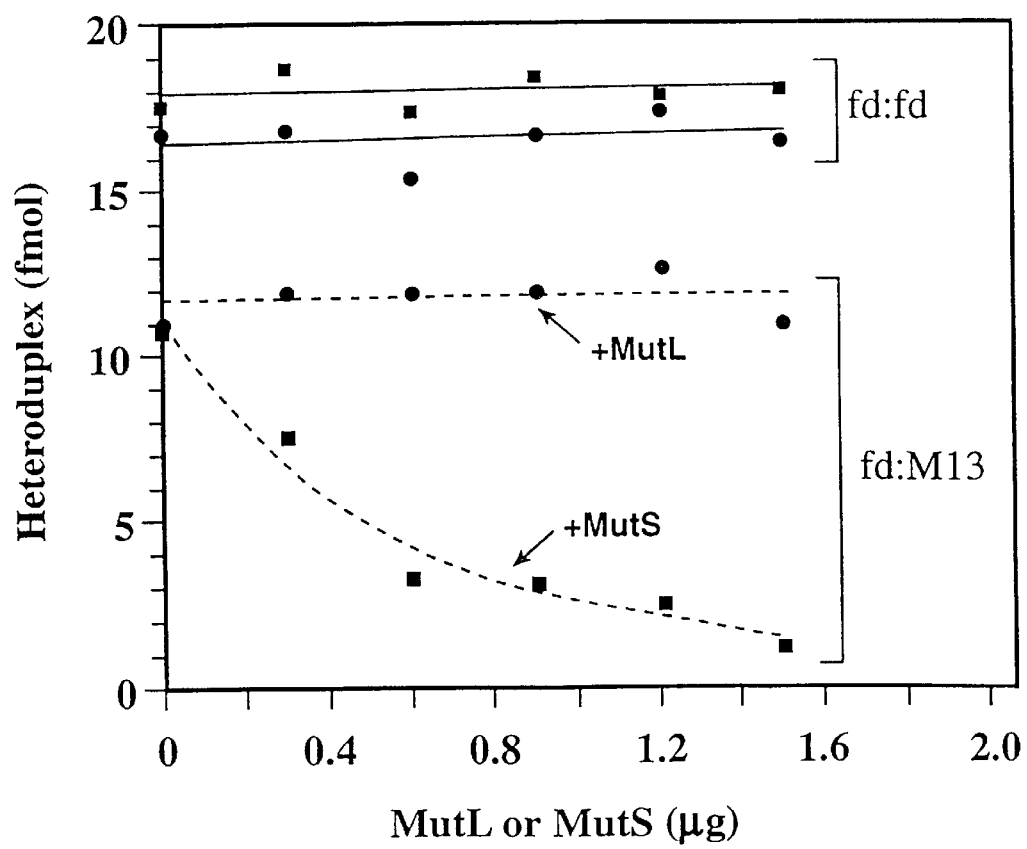
FIG. 7 depicts the effects of MutS and MutL on RecA-catalyzed strand transfer between homologous and quasi-homologous DNA sequences. Solid lines indicate fd-fd strand transfer, while dashed lines correspond to fd-M13 strand transfer. Strand transfer was evaluated in the presence of MutL (solid circles) or MutS (solid squares).

Results of experiments on the effects of MutS and MutL on RecA-catalyzed strand transfer between homologous and quasi-homologous DNA sequences are shown in FIG. 7. Reactions (50 µl) contained 50 MM HEPES (Ph 7.5), 12 Mm MgCl$_2$, 2 mM ATP, 0.4 mM dithiothreitol, 6 mM phosphocreatine, 10 U/ml phosphocreatine kinase, 0.6 nM single-stranded circular DNA (molecules), 7.6 µg RecA protein, 0.54, μg SSB, and MutS or MutL as indicated. Reactions were allowed to preincubate at 37° C. for 10 minutes, strand exchange was initiated by addition of linear duplex fd DNA (Rf DNA linearized by cleavage with HpaI, 0.6 nM final concentration as molecules), and incubation continued for 70 minutes. MutS or MutL was added 1 minute prior to addition of duplex DNA. Sample (50 μl) were quenched by addition of EDTA (25 mM), sodium dodecyl sulphate (0.1%), and proteinase K (150 μg/ml), followed by incubations at 42° C. for 30 minutes.

The presence of MutS or MutL was without significant effect on strand transfer between linear duplex fd DNA and circular fd single-strands, MutS did inhibit strand transfer between quasi-homologous linear duplex fd DNA and M13 single-strands. Similar results were obtained for strand transfer between duplex M13 DNA and single-stranded fd (data not shown) In contrast, MutL alone did not significantly alter the yield of circular duplex product formed by RecA catalyzed strand transfer between these different DNAs.

EXAMPLE 6

MutL Potentiation of MutS Block to Strand Transfer

Figure 8:
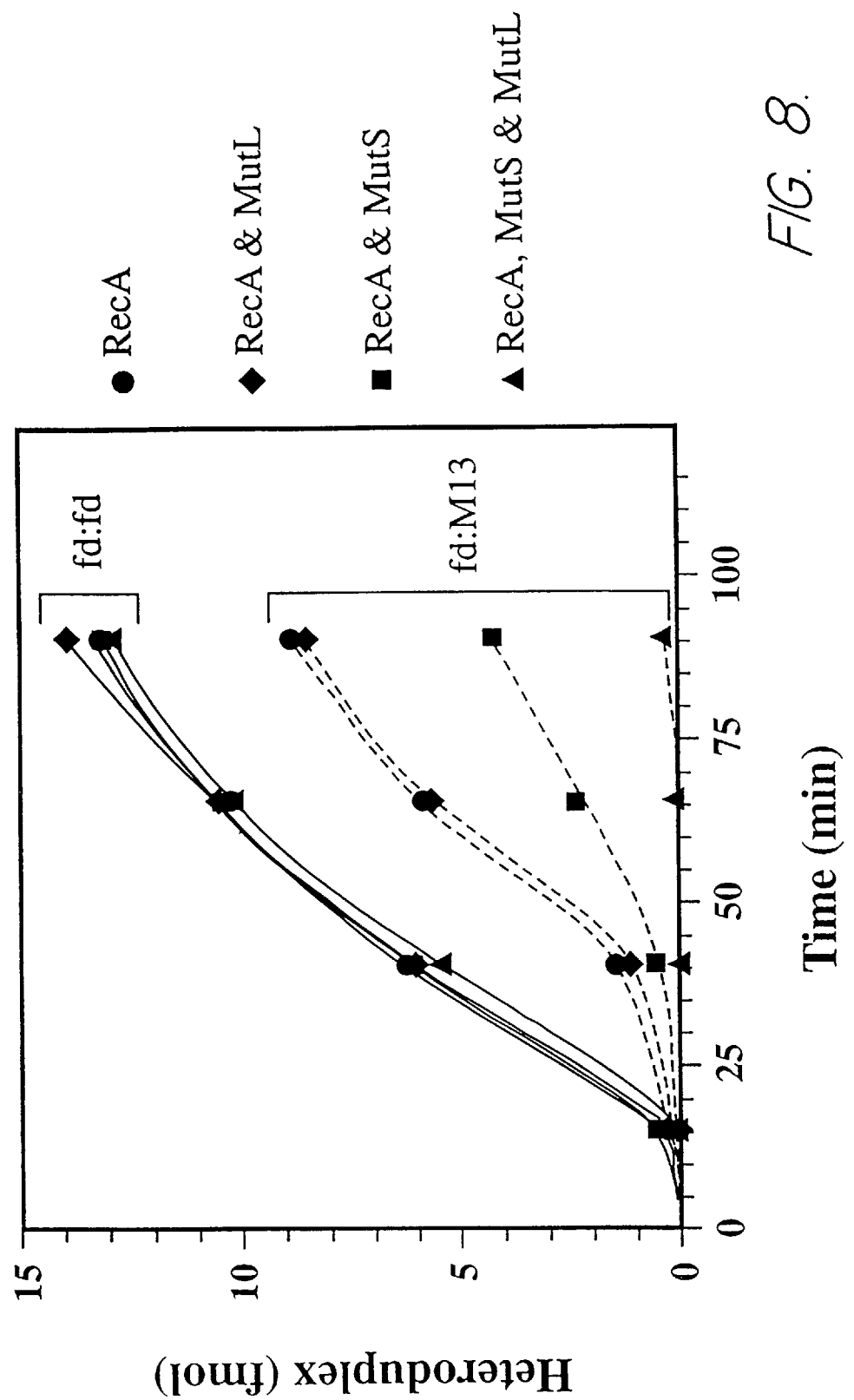
FIG. 8 depicts The MutL potentiation of MutS block to strand transfer in response to mismatched base pairs. Solid lines: fd-fd strand transfer; dashed lines fd-M13 strand transfer; RecA (solid circle); RecA and MutL (solid diamond); RecA and MutS (solid square); RecA, MutL, and MutS (solid triangle).

Results of experiments on the MutL potentiation of the MutS block to strand transfer in response to mismatched base pairs are shown in FIG. 8. Reaction mixtures (210 μl) contained 50 mM HEPES (pH 7.5), 12 mM $MgCl_2$, 2 mM ATP, 0.4 mM dithiothreitol, 6 mM phosphocreatine, 10 U/mL phosphocreatine kinase, 0.6 nM (molecules) single-stranded circular DNA, 32 μg recA protein, and 2.3 μg SSB. Reactions were preincubated for 10 minutes at 37° C. and strand exchange initiated by addition of duplex fd DNA (Rf DNA linearized by cleavage with HpaI, 0.6 nM final concentration as molecules). When present, MutS (2.9 μg) and/or MutL (1.3 μg) were added 1 minute prior to addition of duplex DNA. Samples were removed as indicated times and quenched as described in Example 5.

MutL potentiates the inhibition of heteroduplex formation that is observed with MutS. Formation of full length, circular heteroduplex product is virtually abolished in the presence of MutS and MutL. Heteroduplex formation between perfectly homologous strands occurred readily in the presence of either or both proteins.

EXAMPLE 7

MutS and MutL Block of Branch Migration

Figure 9:
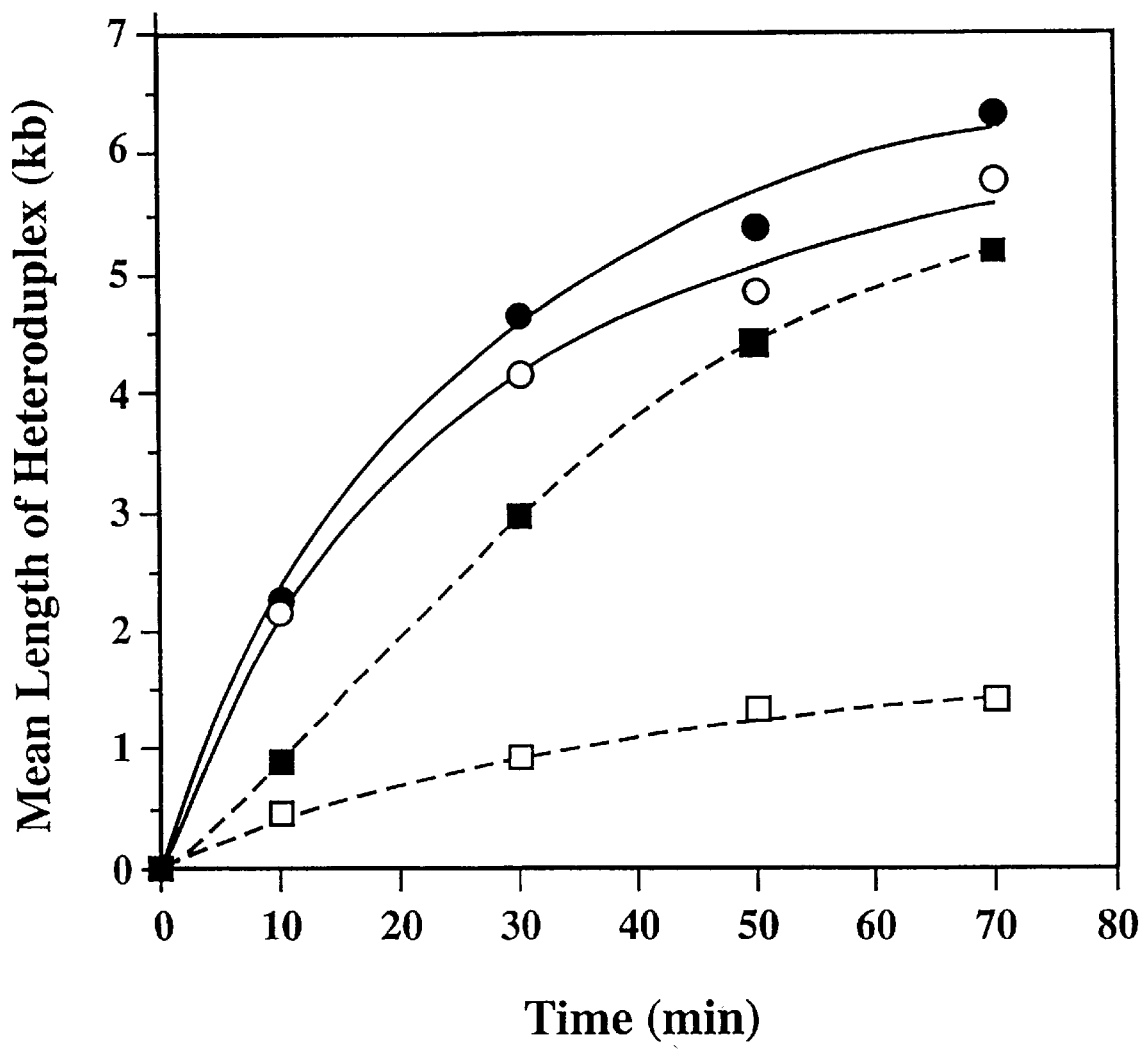
FIG. 9 depicts the MutS and MutL block of branch migration through regions that generate mismatched base pairs. Solid lines: M13-M13 strand transfer; dashed line fd-M13 strand transfer. RecA only (solid circle and square); RecA, MutS, and MutL (open circle and square).

While MutS and MutS along with MutL blocked formation of fully duplex, circular fd-M13 product, some strand transfer did occur in these reactions as demonstrated by the occurrence of strand transfer "intermediates" that migrated more slowly in agarose gels than fully duplex, nicked circular product (data not shown). The nature of these structures was examined using the S1 nuclease procedure of Cox and Lehman to evaluate mean length of stable heteroduplex formation. This analysis is shown in FIG. 9.

Reaction mixtures (510 μl) contained 50 mM HEPES (pH 7.5), 12 mM $MgCl_2$, 2 mM ATP, 0.4 mM dithiothreitol, 6 mM phosphocreatine, 10 U/mL phosphocreatine kinase, 0.6 nM single-stranded circular DNA (molecules), 77 μg RecA protein, 5.5 μg SSB, and when indicated 6.9 μg MutS and 3.2 μg MutL. Reactions were allowed to preincubate at 37° C. for 10 minutes, strand exchange was initiated by addition of linear duplex [$^3$H]M13 DNA (Rf DNA linearized by cleavage with HpaI, 0.6 nM final concentration as molecules). MutS or MutL was added 1 minute prior to addition of M13 duplex DNA. Samples (100 μl) were taken as indicated, quenched with sodium dodecyl sulphate (0.8%), and extracted with phenol:chloroform:isoamyl alcohol (24:24:1) equilibrated with 10 mM Tris-HCl, pH 8.0, 0.1 mM EDTA. The organic phase was back-extracted with 0.5 volume of 50 mM HEPES, pH 5.5. Aqueous layers were combined washed with $H_2O$-saturated ether, and relieved of residual ether by 30 minutes incubation at 37° C. The mean length of stable heteroduplex was then determined using S1 nuclease (10 U/ml) according to Cox and Lehman (Cox, 1981 supra).

Although some strand transfer occurs between fd and M13 DNAs in the presence of MutS and MutL, heteroduplex formation is restricted to about one kilobase of the 6.4 kilobase possible. The MutS and MutL effects on recombination are due, at least in part, to their ability to control branch migration reaction in response to occurrence of mismatched base pairs.

Other embodiments are within the following claims.

---

What is claimed is:

1. A solution comprising the MutL and MutS proteins of *Escherichia coli* and no other protein of a mismatch repair system.

2. A solution comprising homologs of the MutL and MutS proteins of *Escherichia coli* and no other protein of a mismatch repair system.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

C T C G A G A G C T    T                          1 1

( 2 ) INFORMATION FOR SEQ ID NO: 2:

( i ) SEQUENCE CHARACTERISTICS:

(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 2:

CTCGAGAGCT G                                                                                      11

(2) INFORMATION FOR SEQ ID NO: 3:

(i) SEQUENCE CHARACTERISTICS:
(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 3:

ATCGATAGCT T                                                                                       11

(2) INFORMATION FOR SEQ ID NO: 4:

(i) SEQUENCE CHARACTERISTICS:
(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 4:

ATCGAAAGCT T                                                                                       11

(2) INFORMATION FOR SEQ ID NO: 5:

(i) SEQUENCE CHARACTERISTICS:
(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 5:

CTCGAAAGCT T                                                                                       11

(2) INFORMATION FOR SEQ ID NO: 6:

(i) SEQUENCE CHARACTERISTICS:
(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 6:

GTCGACAGCT T                                                                                       11

(2) INFORMATION FOR SEQ ID NO: 7:

(i) SEQUENCE CHARACTERISTICS:
(A) LENGTH: 11 base pairs
(B) TYPE: nucleic acid
(C) STRANDEDNESS: double
(D) TOPOLOGY: linear (xi) SEQUENCE DESCRIPTION: SEQ ID NO: 7:

GTCGAAAGCT T                                                                                       11

(2) INFORMATION FOR SEQ ID NO: 8:

(i) SEQUENCE CHARACTERISTICS:
(A) LENGTH: 11 base pairs
(B) TYPE: nucleic acid ( C ) STRANDEDNESS: double
         ( D ) TOPOLOGY: linear ( x i ) SEQUENCE DESCRIPTION: SEQ ID NO: 8:

CTCGACAGCT G                                                            11

( 2 ) INFORMATION FOR SEQ ID NO: 9:

( i ) SEQUENCE CHARACTERISTICS:
         ( A ) LENGTH: 16 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 9:

GATCCGTCGA CCTGCA                                                       16

( 2 ) INFORMATION FOR SEQ ID NO: 10:

( i ) SEQUENCE CHARACTERISTICS:
         ( A ) LENGTH: 16 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 10:

TGCAGGTCGA CGGATC                                                       16

( 2 ) INFORMATION FOR SEQ ID NO: 11:

( i ) SEQUENCE CHARACTERISTICS:
         ( A ) LENGTH: 16 base pairs
         ( B ) TYPE: nucleic acid
         ( C ) STRANDEDNESS: single
         ( D ) TOPOLOGY: linear ( x i ) SEQUENCE DESCRIPTION: SEQ ID NO: 11:

TGCAGGTTGA CGGATC                                                       16

( 2 ) INFORMATION FOR SEQ ID NO: 12:

( i ) SEQUENCE CHARACTERISTICS:
         ( A ) LENGTH: 11 base pairs
         ( B ) TYPE: nucleic acid
         ( C ) STRANDEDNESS: double
         ( D ) TOPOLOGY: linear ( x i ) SEQUENCE DESCRIPTION: SEQ ID NO: 12:

AAGCTTTCGA G                                                            11